(12) United States Patent
Au et al.

(10) Patent No.: US 8,157,833 B2
(45) Date of Patent: Apr. 17, 2012

(54) TROCARS WITH ADVANCED FIXATION

(75) Inventors: Gigi Au, Monterey Park, CA (US);
Jeremy J. Albrecht, Ladera Ranch, CA (US); Charles C. Hart, Summerville, SC (US); Gary M. Johnson, Mission Viejo, CA (US); John R. Brustad, Dana Point, CA (US)

(73) Assignee: Applied Medical Resources Corporation, Racho Santa Margarita, CA (US)

( * ) Notice: Subject to any disclaimer, the term of this patent is extended or adjusted under 35 U.S.C. 154(b) by 1112 days.

(21) Appl. No.: 11/270,181

(22) Filed: Nov. 9, 2005

(65) Prior Publication Data

US 2007/0106319 A1    May 10, 2007

(51) Int. Cl.
*A61M 29/00* (2006.01)
*A61B 17/34* (2006.01)

(52) U.S. Cl. ........................................ 606/191; 606/105
(58) Field of Classification Search .................. 606/184; 604/105, 164.04; 411/36, 38
See application file for complete search history.

(56) References Cited

U.S. PATENT DOCUMENTS

| | | | |
|---|---|---|---|
| 3,817,251 A | 6/1974 | Hasson | |
| 3,970,090 A | 7/1976 | Loiacono | |
| 4,762,130 A | 8/1988 | Fogarty et al. | |
| 5,122,122 A | 6/1992 | Allgood | |
| 5,147,316 A | 9/1992 | Castillenti | |
| 5,176,697 A | 1/1993 | Hasson et al. | |
| 5,217,441 A | 6/1993 | Shichman | |
| 5,257,975 A * | 11/1993 | Foshee | 604/105 |
| 5,271,380 A | 12/1993 | Riek et al. | |
| 5,330,497 A | 7/1994 | Freitas et al. | |
| 5,330,501 A | 7/1994 | Tovey et al. | |
| 5,352,211 A | 10/1994 | Merskelly | |
| 5,403,336 A | 4/1995 | Kieturakis et al. | |
| 5,407,433 A | 4/1995 | Loomas | |

(Continued)

FOREIGN PATENT DOCUMENTS

DE    200 12 003 U1    10/2000

(Continued)

OTHER PUBLICATIONS

European Patent Office, The International Search Report and the Written Opinion of the International Searching Authority for PCT Application No. PCT/US2006/060212 mailed Mar. 21, 2007.

(Continued)

*Primary Examiner* — Gary Jackson
*Assistant Examiner* — Jonathan Hollm
(74) *Attorney, Agent, or Firm* — John F. Heal; David G. Majdali

(57) ABSTRACT

A trocar fixation device includes a cannula and an elongate tube mounted onto and coupled to the exterior surface of the cannula with the distal end of the cannula extending distally beyond the distal end of the elongate tube. The elongate tube includes a plurality of slits cut at an angle to a longitudinal axis of the elongate tube. The trocar fixation device is activated by rotating the proximal-end region of the elongate tube in a first direction and is deactivated by rotating the proximal-end region of the elongate tube in a second direction, opposite to the first direction. Activation of the trocar fixation device compresses the material positioned between adjacent slits and forces the material radially outwardly, away from the exterior surface of the cannula, thereby forming ridges. Deactivation of the trocar fixation device returns the exterior surface of the elongate tube to a substantially smooth condition.

62 Claims, 22 Drawing Sheets

U.S. PATENT DOCUMENTS

| | | | |
|---|---|---|---|
| 5,411,483 A | 5/1995 | Loomas et al. | |
| 5,445,615 A | 8/1995 | Yoon | |
| 5,472,429 A | 12/1995 | Yoon | |
| 5,501,695 A * | 3/1996 | Anspach et al. | 606/232 |
| 5,653,690 A | 8/1997 | Booth et al. | |
| 5,697,913 A | 12/1997 | Sierocuk et al. | |
| 5,814,058 A | 9/1998 | Carlson et al. | |
| 5,836,913 A | 11/1998 | Orth et al. | |
| 5,893,850 A * | 4/1999 | Cachia | 606/326 |
| 6,099,506 A * | 8/2000 | Macoviak et al. | 604/173 |
| 6,432,085 B1 | 8/2002 | Stellon et al. | |
| 6,524,283 B1 | 2/2003 | Hopper et al. | |
| 6,719,509 B1 * | 4/2004 | Huang et al. | 411/32 |
| 6,808,492 B2 | 10/2004 | Snyder | |
| 7,691,089 B2 | 4/2010 | Gresham | |
| 2002/0026137 A1 * | 2/2002 | Yencho et al. | 604/8 |
| 2004/0068228 A1 | 4/2004 | Cunningham | |
| 2005/0143827 A1 * | 6/2005 | Globerman et al. | 623/17.16 |

FOREIGN PATENT DOCUMENTS

| | | |
|---|---|---|
| FR | 2 810 555 A1 | 12/2001 |
| WO | WO 01/89398 A | 11/2001 |
| WO | WO 03/011143 A | 2/2003 |

OTHER PUBLICATIONS

The International Bureau of WIPO, The International Preliminary Report on Patentability for PCT Application No. PCT/US2006/060212 dated May 14, 2008.

* cited by examiner

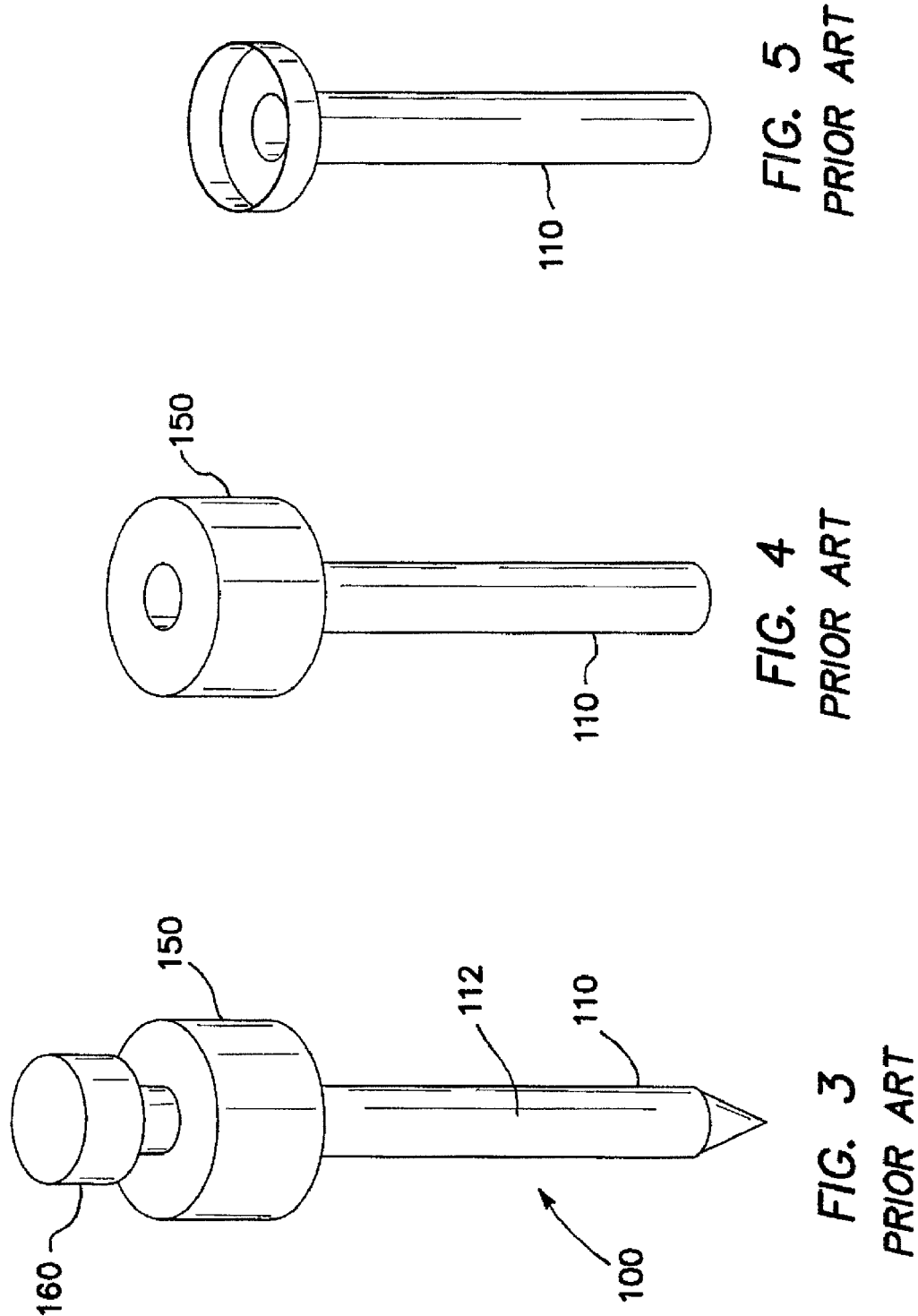

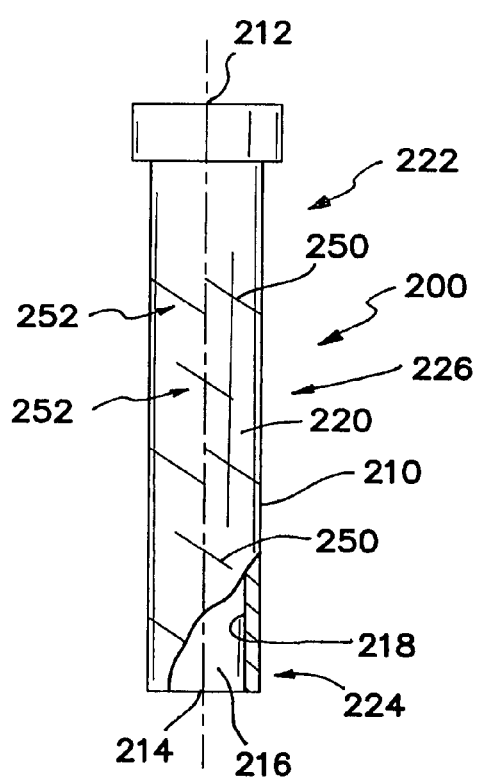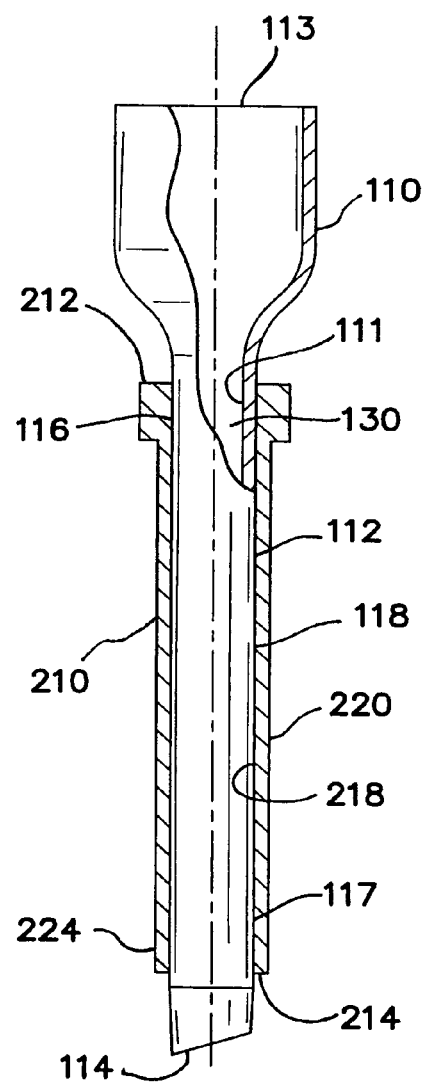
FIG. 13
FIG. 14

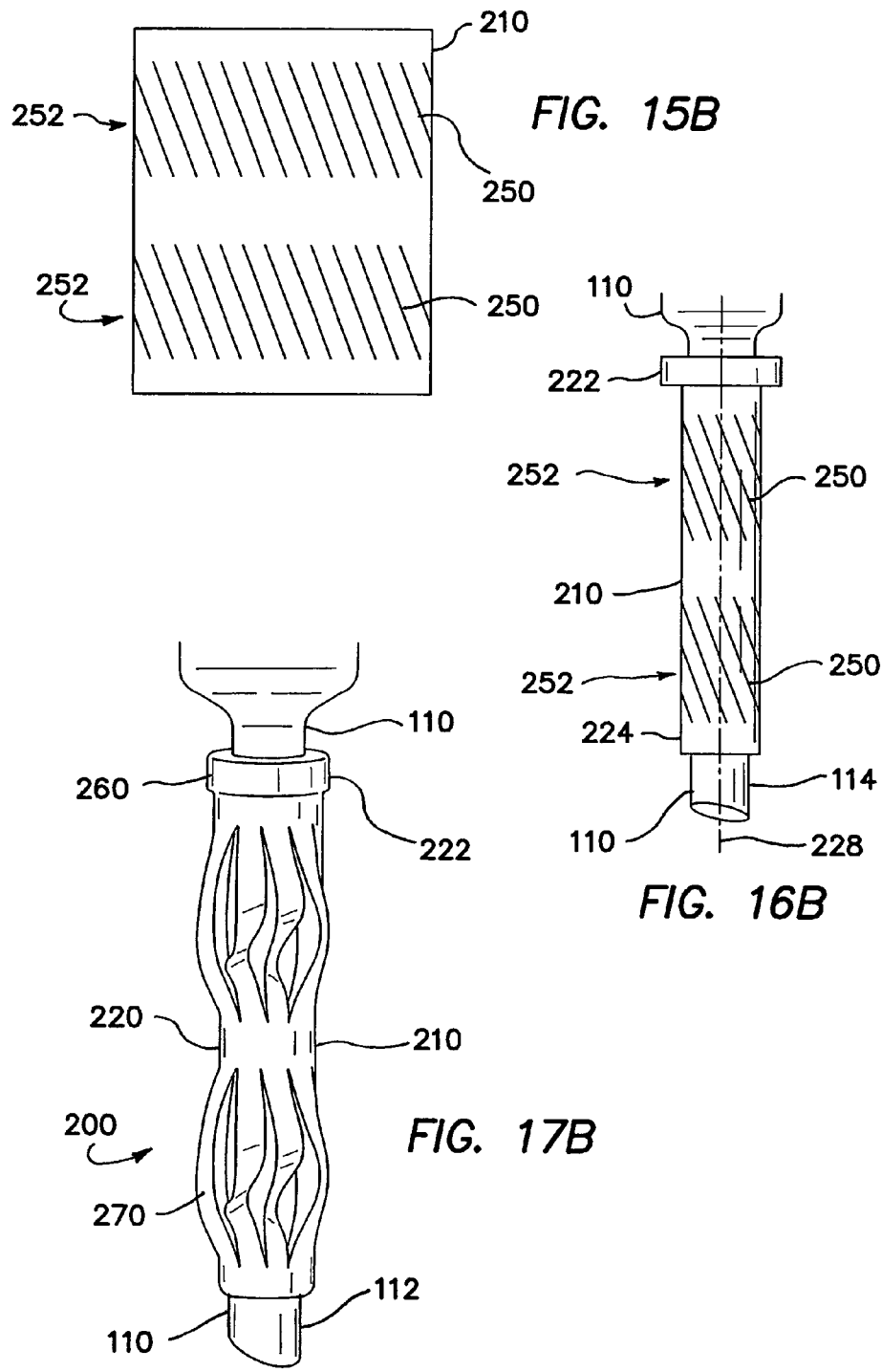

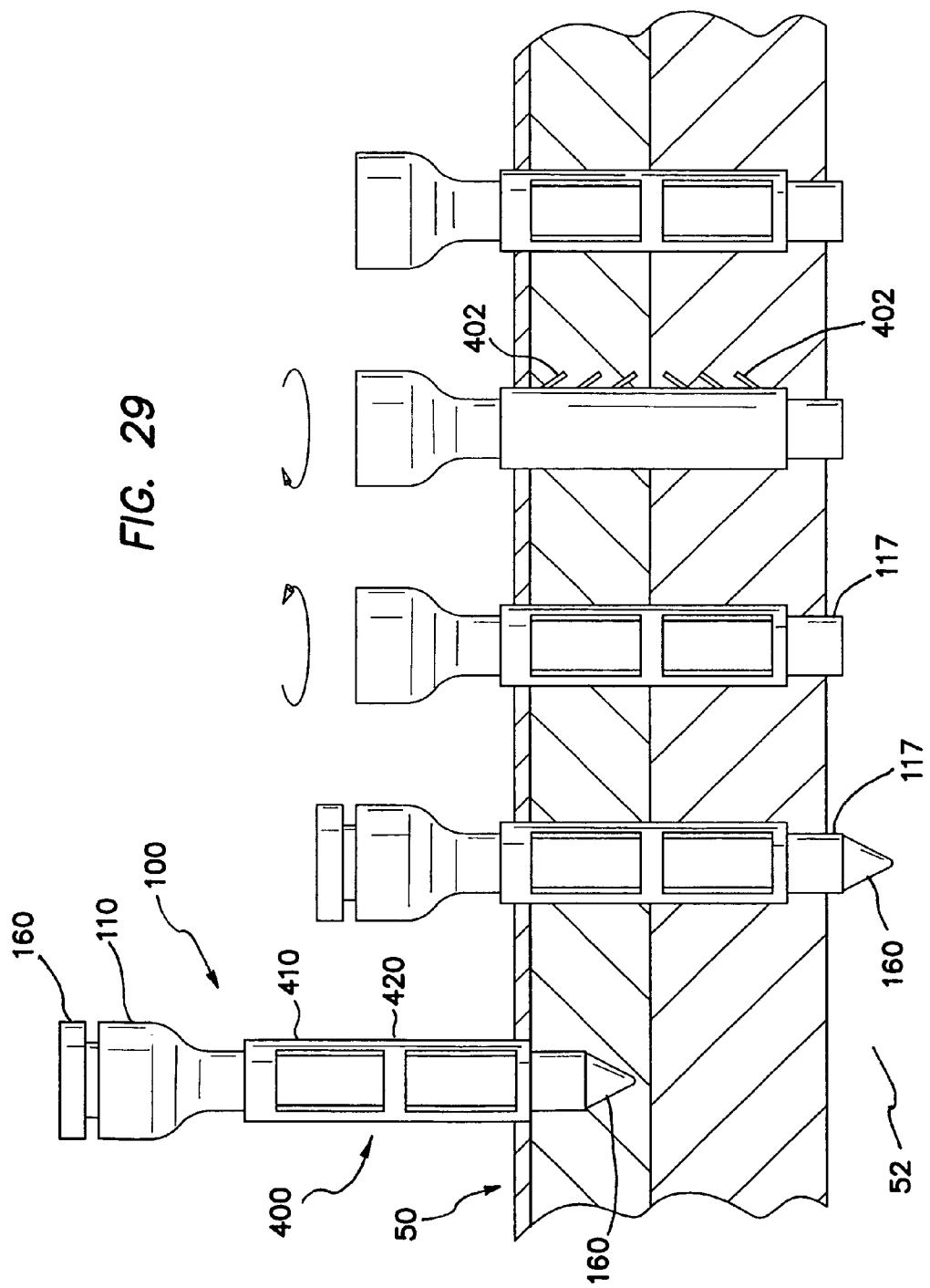

TROCARS WITH ADVANCED FIXATION

BACKGROUND

This invention relates generally to trocar systems including cannulas and, more specifically, to trocars having advanced fixation capabilities.

Trocar systems have been of particular advantage in facilitating less invasive surgery across a body wall and within a body cavity. This is particularly true in abdominal surgery where trocars have provided a working channel across the abdominal wall to facilitate the use of instruments within the abdominal cavity.

Trocar systems typically include a cannula, which provides the working channel, and an obturator that is used to place the cannula across a body wall, such as the abdominal wall. The obturator is inserted into the working channel of the cannula and pushed through the body wall with a penetration force of sufficient magnitude to result in the penetration of the body wall. Once the cannula has traversed the body wall, the obturator can be removed.

With the cannula in place in the body wall, various instruments may be inserted into the body cavity, such as the abdominal cavity through the cannula. One or more cannulas may be used during a procedure. During the procedure, the surgeon manipulates the instruments in the cannulas, sometimes using more than one instrument at a time. The manipulation of an instrument by a surgeon may cause frictional forces between the instrument and the cannula in which the instrument is inserted, which in turn may result in movement of the cannula in an inward or outward direction within the body wall. If the cannula is not fixed in place, there is a potential that proximal or distal motions of the instruments through the cannula may cause the cannula to slip out of the body wall or to protrude further into the body cavity, possibly leading to injury to the patient.

The surfaces of the cannula associated with a trocar are generally smooth. The smoothness of a cannula surface makes placement of the cannula through a body wall relatively easy and safe. However, a smooth cannula may not have the desired retention characteristics once the cannula has been placed through a body wall. This may present problems as instruments and specimens are removed from a body cavity through the cannula and the associated seal systems of the trocar. It is highly desirable for a cannula to remain fixed in the most appropriate position once placed.

Many solutions to the issue of trocar-cannula fixation or stabilization have been formed. These solutions include an inflatable balloon attached- to the distal portion of the cannula, raised threads or raised rings associated with the outer surface of the cannula, mechanically deployable enlarging portions arranged at the distal end of a cannula and suture loops or hooks associated with the proximal end of the trocar. These solutions have provided some degree of fixation or stabilization. However, there remains a need for a fixation or stabilization device that may be used with a variety of trocar-cannulas and addresses the additional requirements associated with developing laparoscopic surgical procedures and techniques. More particularly, the cannula must provide sufficient retention force to be able to anchor itself into the abdominal wall without slipping in our out. However, the cannula should also be capable of being inserted and removed with minimal force in order to minimize trauma on body tissues, such as abdominal tissues.

SUMMARY OF THE INVENTION

The invention is directed to trocars that are used in laparoscopic surgeries and, more specifically, to means for fixating a cannula in a body wall during a laparoscopic surgery. The trocar fixation device includes an elongate tube that is mountable onto the exterior of a cannula. The elongate tube includes a proximal end, a distal end, a lumen extending between the proximal end and the distal end, an interior surface, an exterior surface, a proximal-end region, a distal-end region, a central region positioned between the proximal-end region and the distal-end region, and a plurality of slits positioned about a periphery of the central region of the elongate tube and forming a row of slits.

In one aspect, the trocar fixation device also includes a cannula having an interior surface, an exterior surface, a proximal end, a distal end, a proximal-end region, a distal-end region, and a central region that is positioned between the proximal-end region and the distal-end region. The elongate tube is mountable onto the exterior surface of the cannula. In another aspect, the slits are cut at an angle to a longitudinal axis of the elongate tube. The cannula is positioned within the lumen of the elongate tube such that the distal end of the cannula extends distally beyond the distal end of the elongate tube. At least a portion of the distal-end region of the elongate tube is coupled to the exterior surface of the cannula forming a substantially gas-tight seal between the elongate tube and the cannula. In one aspect, the slits are cut at an angle of between about 20° and about 70° to the longitudinal axis of the elongate tube. In another aspect, the slits have a length of between about 8.0 mm and about 35.0 mm. In a further aspect, the trocar fixation device is activated by rotating the proximal-end region of the elongate tube in a first direction in relation to the cannula and about a longitudinal axis of the elongate tube and the trocar fixation device is deactivated by rotating the proximal-end region of the elongate tube in a second direction, opposite to the first direction, in relation to the cannula and about the longitudinal axis of the elongate tube. Activation of the trocar fixation device compresses the material positioned between adjacent slits and forces the material between adjacent slits radially outwardly, away from the exterior surface of the cannula, thereby forming ridges in the exterior surface of the elongate tube. Deactivation of the trocar fixation device returns the exterior surface of the elongate tube to a substantially smooth condition.

In another embodiment of the invention, a trocar fixation device includes a cannula having an interior surface, an exterior surface, a proximal end, a distal end, a proximal-end region, a distal-end region, and a central region that is positioned between the proximal-end region and the distal-end region. The trocar fixation device also includes at least one flap coupled to the exterior surface of the cannula within the central region of the cannula. Additionally, the trocar fixation device includes an elongate tube rotatably mounted onto the cannula and over the at least one flap. The elongate tube includes a proximal end, a distal end, a lumen extending between the proximal end and the distal end, an interior surface, an exterior surface, a proximal-end region, a distal-end region, a central region that is positioned between the proximal-end region and the distal-end region, and at least one opening extending between the interior surface and the exterior surface of the elongate tube. In a free, activated state, the at least one flap biases radially outwardly from the cannula and in a constrained, deactivated state, the at least one flap is positioned between the cannula and the elongate tube and maintained substantially parallel to the second, exterior surface of the cannula. The at least one opening in the elongate tube is sized and positioned such that rotation of the elongate tube in a first direction about the cannula exposes the at least one flap in its entirety through the opening and allows the at least one flap to activate.

In one aspect, the elongate tube possesses sufficient stiffness to collapse the at least one flap during deactivation of the fixation device. In another aspect, continued rotation of the elongate tube in the first direction causes a first edge of the at least one opening to be positioned under a portion of the at least one activated flap, thereby substantially supporting the at least one flap in the activated state. In a further aspect, rotating the elongate tube in a second direction, substantially opposite the first direction, about the cannula removes support for the at least one flap and continued rotation of the elongate tube in the second direction causes a second edge of the at least one opening to slide over the at least one flap and to collapse and deactivate the at least one flap.

These and other features of the invention will become more apparent with a discussion of the various embodiments in reference to the associated drawings.

DESCRIPTION OF THE DRAWINGS

FIG. 3 is a perspective view of a prior art assembled trocar and obturator;

FIG. 4 is a perspective view of a prior art assembled trocar without an obturator;

FIG. 5 is a perspective view of a prior art cannula;

FIG. 13 is a side view of a trocar fixation device of the present invention;

FIG. 14 is a side view, partially in cross-section, of a trocar fixation device of the present invention depicting the trocar fixation device mounted onto a cannula;

FIGS. 15a-15i includes flat pattern layouts of trocar fixation devices of the present invention;

FIGS. 16a-16i includes trocar fixation devices of the present invention mounted onto cannulas with the trocar fixation devices in a deactivated condition;

FIGS. 17a-17h includes trocar fixation devices of the present invention mounted onto cannula with the trocar fixation device in an activated condition;

FIG. 29 is a side view, partially in cross-section, depicting the trocar fixation device of FIG. 24 and progressive steps of inserting the trocar into the body wall of a patient, activating the trocar fixation device and deactivating the trocar fixation device

DESCRIPTION

Figure 1:
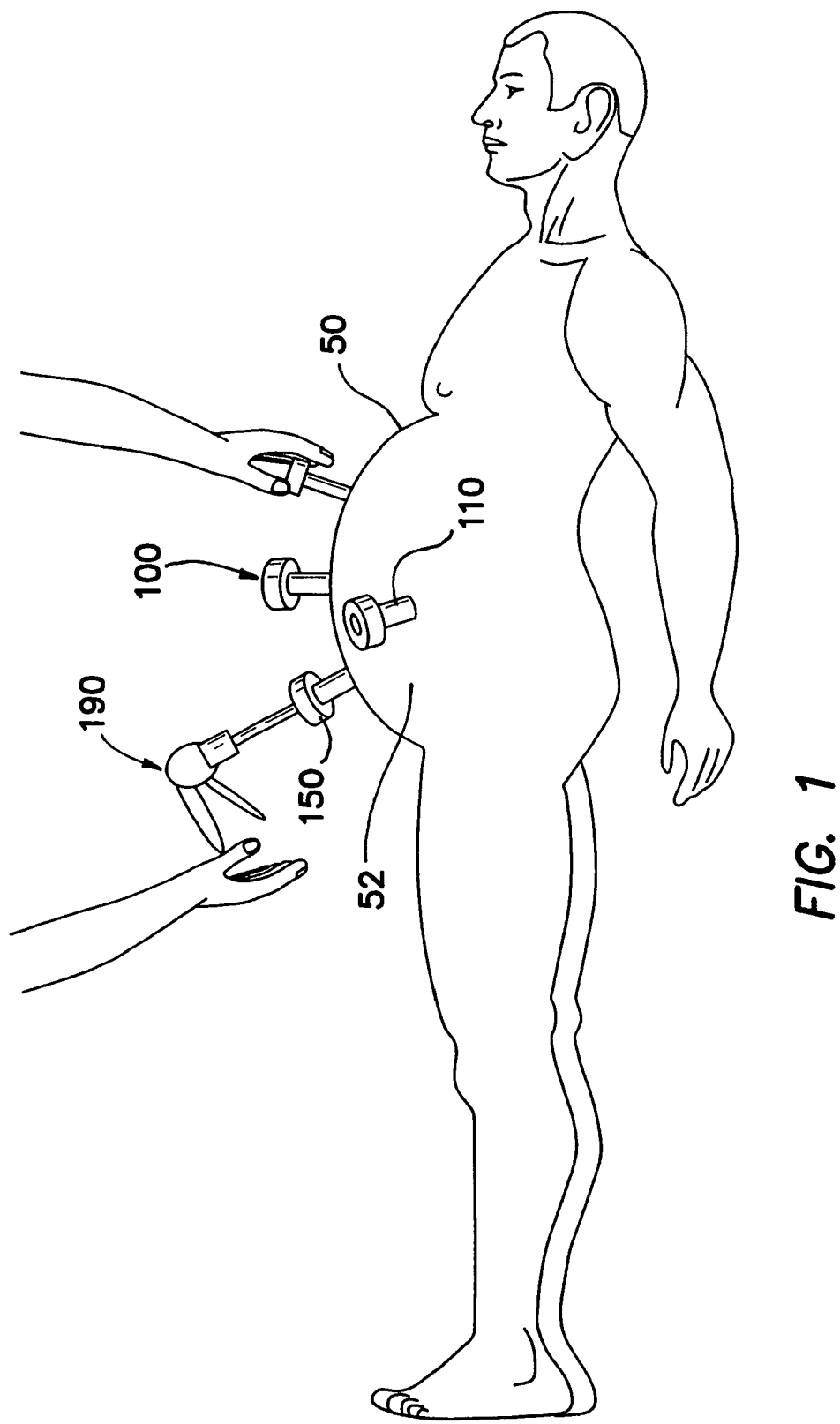
FIG. 1 is a side view of a laparoscopic surgical procedure.
Figure 2:
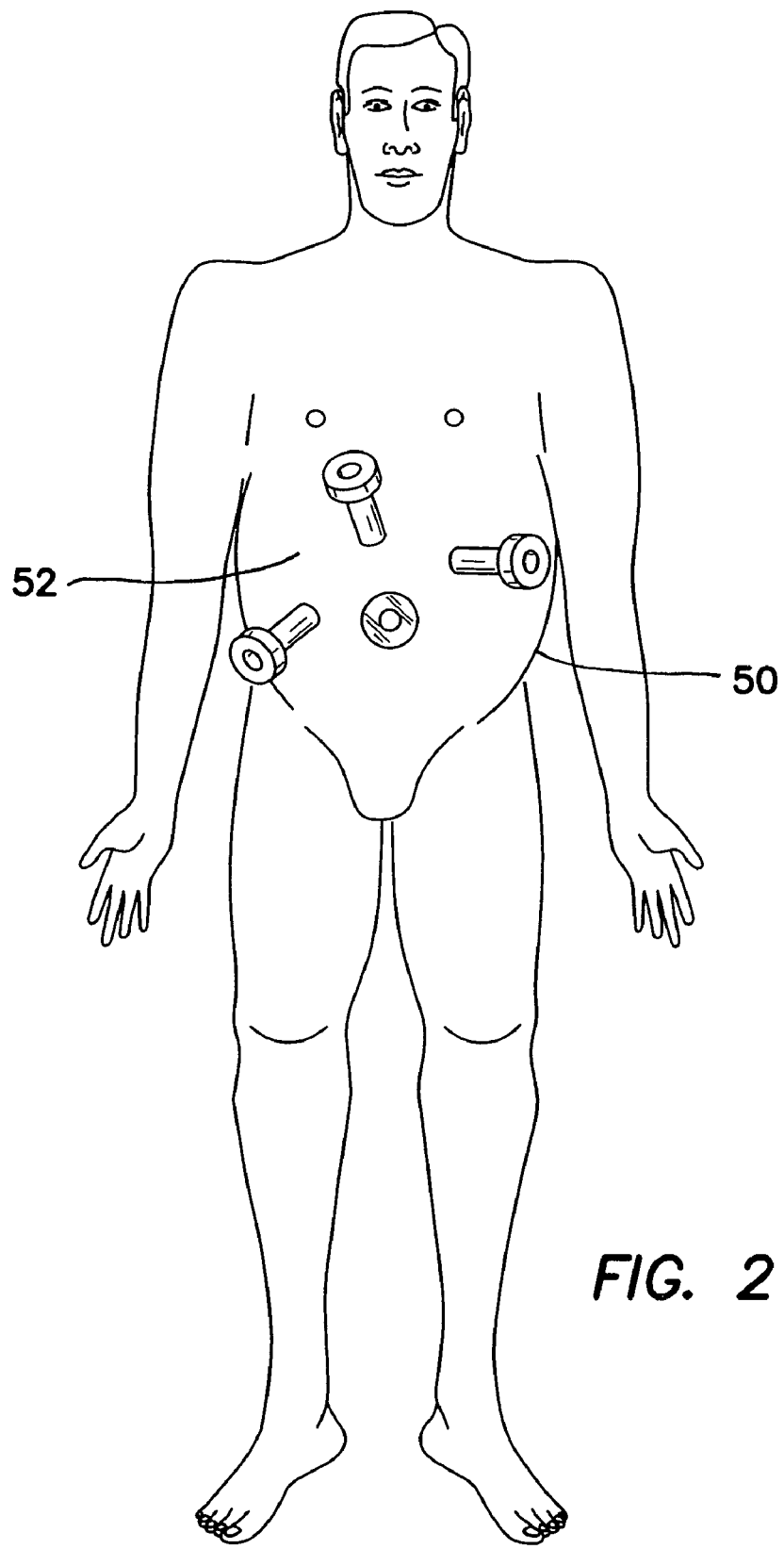
FIG. 2 is a top view of a laparoscopic surgical procedure showing placement of trocars.

With reference to FIGS. 1 and 2, a typical laparoscopic procedure is illustrated where a plurality of trocars 100 are placed through a body wall 50, such as an abdominal wall, and into a body cavity 52, such as an abdominal cavity. The body cavity 52 is insufflated, or inflated with gas, to distend the body wall 50 and provide a working space for the laparoscopic procedure. The trocars 100 each include a cannula 110 and a seal 150. Positive pressure is maintained within the body cavity 52 by the seal 150 associated with the cannula 110. In addition, the cannula 110 must fit tightly through the incision through the body wall 50 and maintain a gas-tight seal against adjacent tissue. If positive pressure is lost, either through the seal 150 associated with the cannula 110 or the seal between the cannula and the adjacent tissue, the procedure may be compromised.

As the body cavity 52 is inflated, the body wall 50 may be greatly distended. The access sites may tend to enlarge under the distention of the body wall 50 and compromise the positioning and sealing of the cannula 110. As stated above, the manipulation of instruments 190 used through the trocars 100 may result in movement of the cannulas 110 in either a proximal or distal direction and/or rotation of the cannulas 110 within the access site through the body wall 50. As this occurs, some liquefaction may take place and the preferred relationship between the cannula 110 and the body tissue may be compromised.

Referring now to FIGS. 3-7, a typical assembled trocar 100 is shown having a cannula 110, a seal housing 150 and an obturator 160. The cannula 110 typically has a smooth exterior surface 112 so that it may be inserted through the body wall 50 easily. The seal housing 150 contains a seal system that prevents retrograde gas-flow. The obturator 160 is a cutting or piercing instrument that creates the pathway through the body wall 50 through which the cannula 110 follows. Surgical obturators 160 are generally sized and configured to create a defect in tissue that is appropriate for the associated cannula 110. However, the defect may have a tendency to enlarge during a surgical procedure as the trocar 100 or cannula 110 is manipulated. As an instrument 190 is urged distally and proximally or inserted and withdrawn, the cannula 110 may move or even be inadvertently withdrawn due to the friction between the instrument 190 and the seal 150 of the trocar housing.

Figure 8:
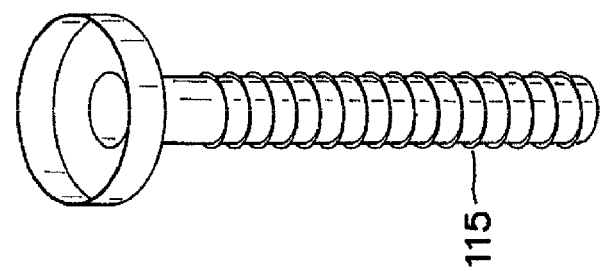
FIG. 8 is a perspective view of a prior art threaded cannula.
Figure 7:
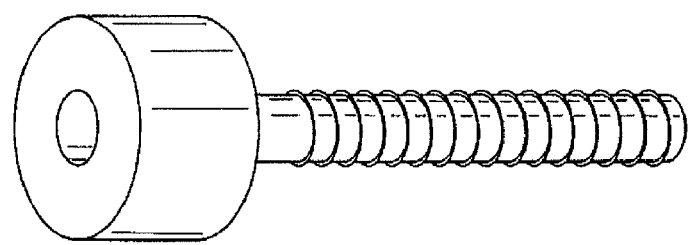
FIG. 7 is a perspective view of a prior art threaded cannula and housing.
Figure 6:
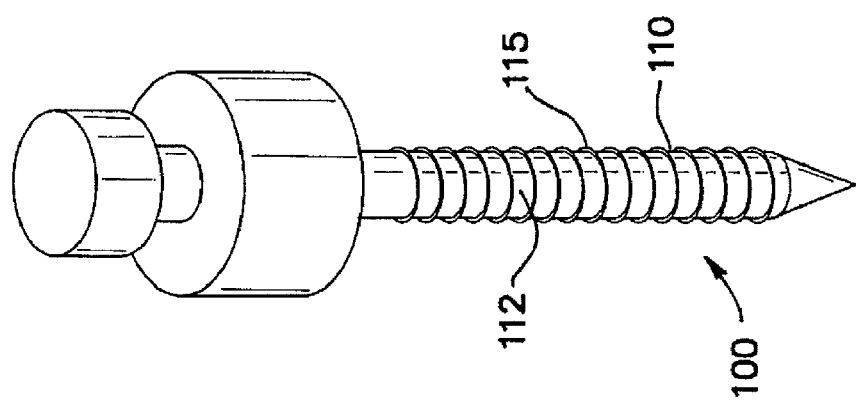
FIG. 6 is a perspective view of a prior art assembled threaded trocar and obturator.
Figures 9, 10:
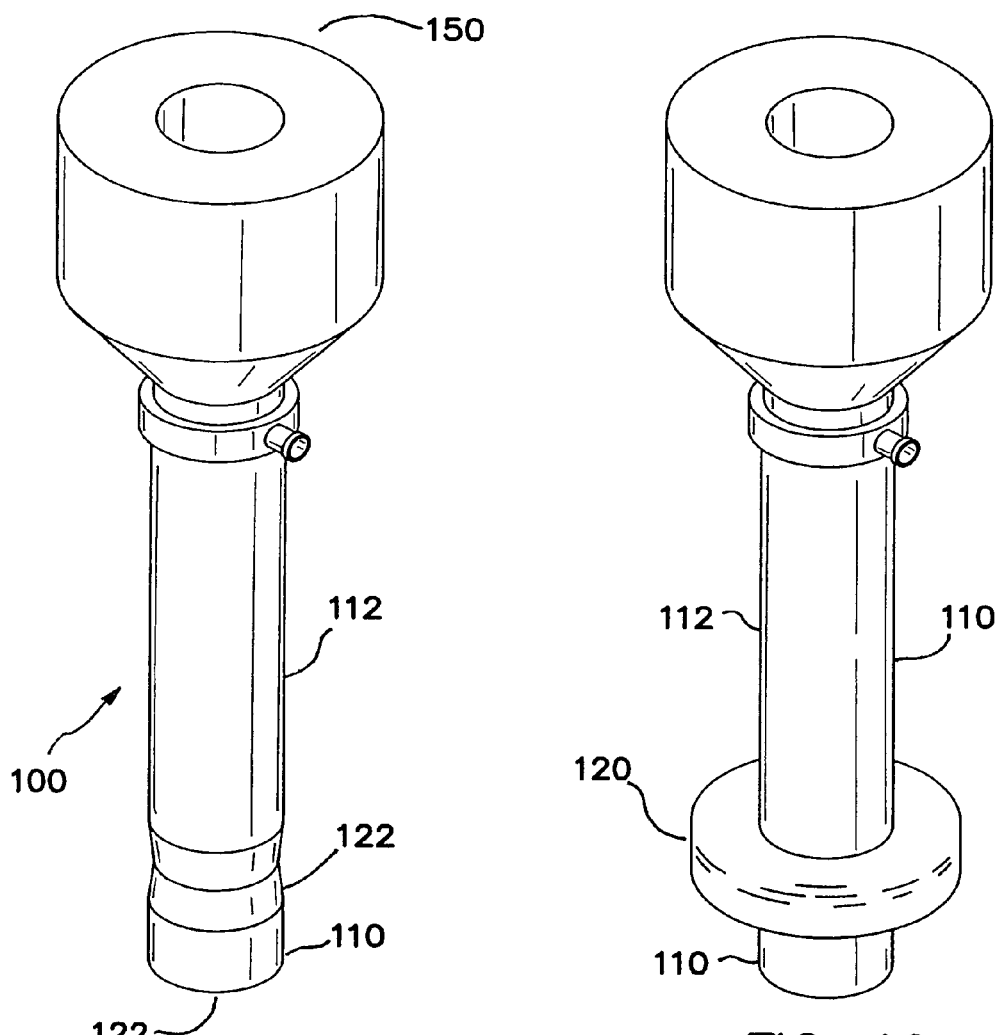
FIG. 9 is a perspective view of a prior art cannula having an uninflated balloon at the distal end.
FIG. 10 is a perspective view of a prior art cannula having an inflated balloon at the distal end.
Figure 11:
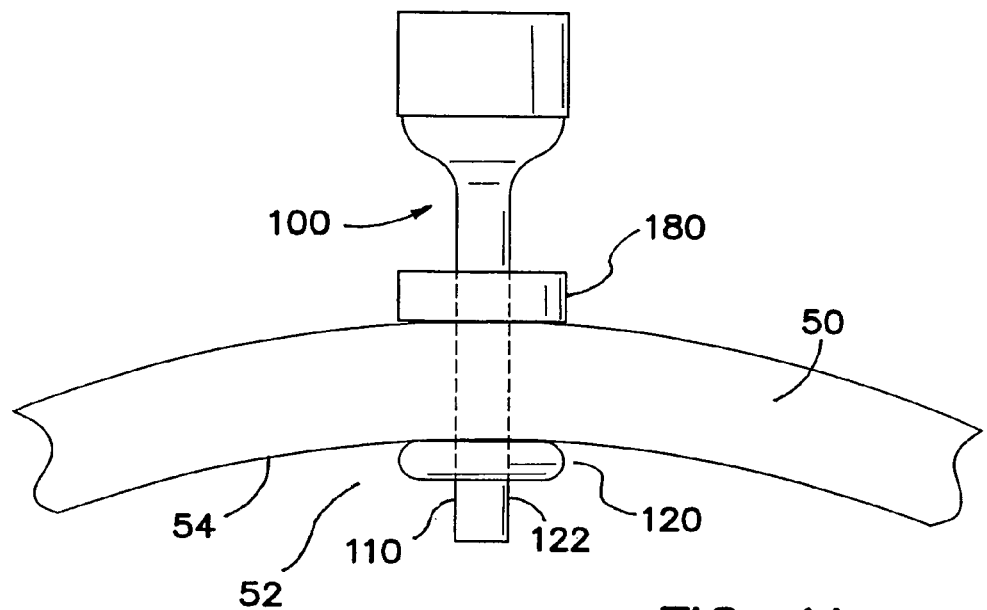
FIG. 11 illustrates a prior art trocar-cannula having a distal retention balloon placed through a body wall in a first position.
Figure 12:
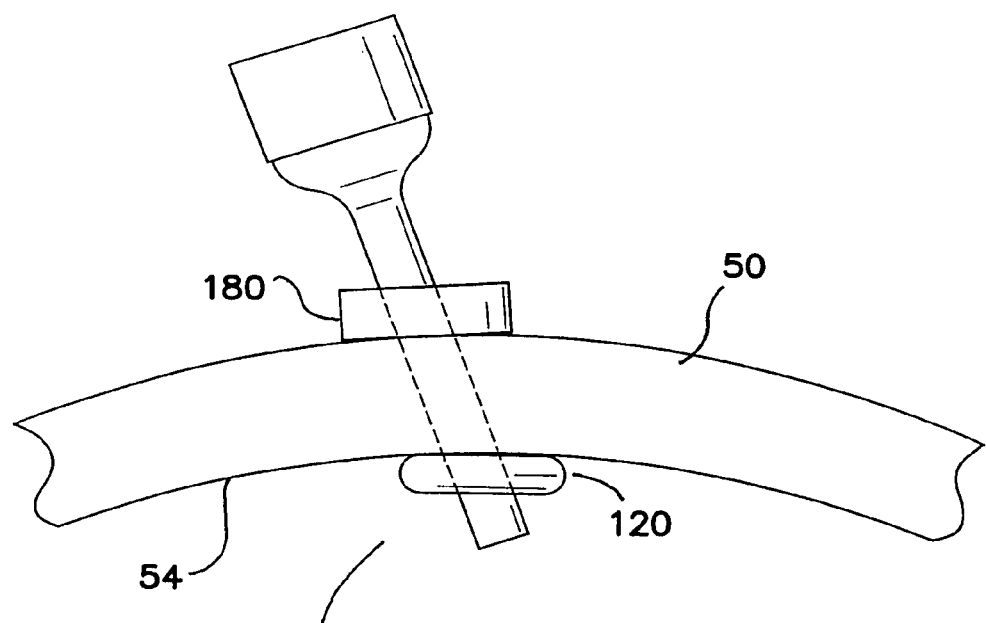
FIG. 12 illustrates a prior art trocar-cannula having a distal retention balloon placed through a body wall in a second position.

With specific reference to FIGS. 6-8, a trocar 100 or access device is shown where the exterior surface 112 of the cannula 110 includes a plurality of raised features 115. These raised features 115 are sized and configured to increase resistance to proximal and distal motion as instruments 190 are maneuvered and especially as specimens are removed through the trocar 100. The prior art includes either sequential raised rings or a raised coarse-thread 115. While the rings or threads 115 of the prior art may stabilize the cannula 110 to some degree, they do not necessarily seal the cannula 110 against the adjacent tissue of a body wall 50. There can be substantial gas loss associated with the use of these systems. The raised rings or threads 115 also increase the insertion force required to penetrate a body wall 50 and may damage delicate body-wall tissue or cause bleeding from the insertion site. The insertion force may be reduced in the instance of a continuous coarse thread 115 in comparison to a sequence of discrete raised rings or features as a threaded cannula 110 may actually be "screwed" into the tissue defect in accordance with the thread direction and pitch, rather than pushed through without appropriate rotation.

With reference to FIGS. 9-12, a surgical access device, or trocar 100, according to prior art includes a cannula 110 having an inflatable balloon 120 associated with the distal-end portion 122 of the cannula. The balloon 120 is sized and configured to fit snugly around the cannula 110 in the uninflated condition. The balloon 120 is inflated after the cannula 110 is properly placed through the body wall 50 and into the body cavity 52. The balloon 120 is generally held against the interior surface 54 of the body wall 50 by a counter-force that is associated with a sliding counter-force member 180. The sliding counter-force member is associated with the proximal portion of the cannula 110. The balloons 120 associated with the devices of the prior art are typically "thick-walled" structures constructed as part of the cannula 110. The balloon 120 is generally bonded to the distal-end portion 122 of the cannula 110 and an inflation channel or lumen is provided within the wall of the cannula. This construction can be complicated and expensive. Additionally, this construction requires that the cannula 110 and associated balloon 120 be inserted whether or not the balloon is required or used.

Referring to FIGS. 13-14, one embodiment of the fixation device 200 of the present invention includes a flexible elongate tube 210 having a first, proximal end 212, a second, distal end 214, a lumen 216 extending between the proximal end and the distal end, a first, interior surface 218 and a second, exterior surface 220. The elongate tube 210 may also include a first, proximal-end region 222, a second, distal-end region 224, and a central region 226 that is positioned between the proximal-end region and the distal-end region. The fixation device 200 may be used with existing trocars 100 and cannulas 110 with no need to alter the cannulas 110, resulting in a fixation device 200 that may be packaged separately from the cannula 110 and placed on the cannula as needed.

The cannula 110 includes a first, interior surface 111, a second, exterior surface 112, a first, proximal end 113, a second, distal end 114, a lumen 130 extending between the proximal end and the distal end, a first, proximal-end region 116, a second, distal-end region 117, and a central region 118 that is positioned between the proximal-end region and the distal-end region. The elongate tube 210 may be slipped over the second, exterior surface 112 of a cannula 110. More particularly, in use the second, distal end 114 of the cannula 110 is inserted into the lumen 216 of the elongate tube 210 from the first, proximal end 212 of the elongate tube and advanced distally through the elongate tube at least until the second, distal end 114 of the cannula extends beyond the second, distal end 214 of the elongate tube. At least a portion of the second, distal-end region 224 of the elongate tube 210 is coupled to the second, exterior surface 112 of the cannula 110 to form a gas-tight seal between the elongate tube and the cannula. In one embodiment, the second, distal-end region 224 of the elongate tube 210 is coupled to the second, distal-end region 117 of the cannula 110. In another embodiment, the second, distal-end region 224 of the elongate tube 210 is coupled to the central region 118 of the cannula. The elongate tube 210 may be coupled to the cannula 110 by bonding, mechanical means, a press seal, or by any other means that is well known in the art.

Figure 15A:
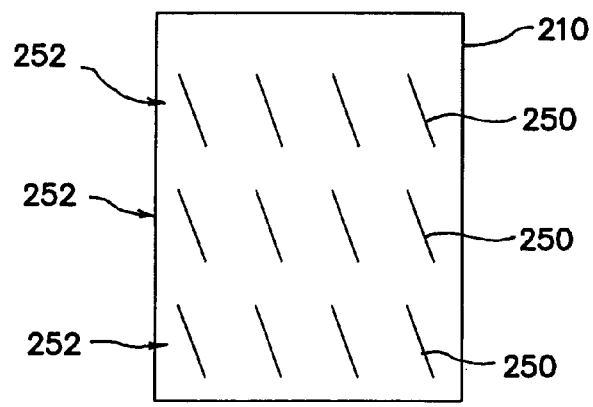
Figure 16A:
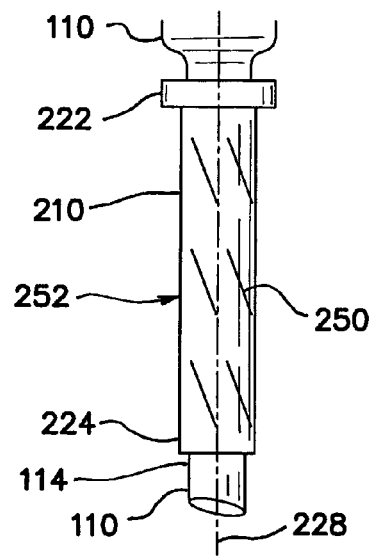
Figure 17A:
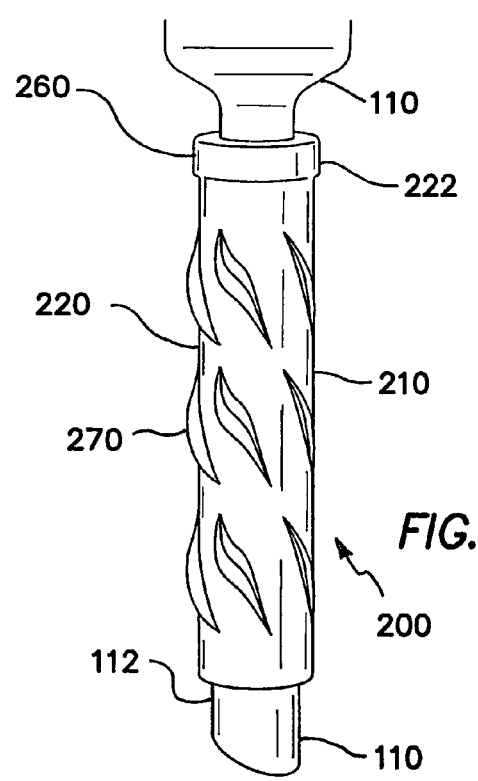
Figure 15C:
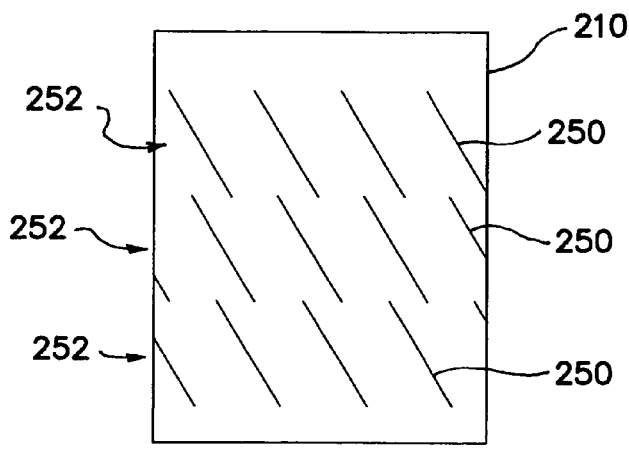
Figure 16C:
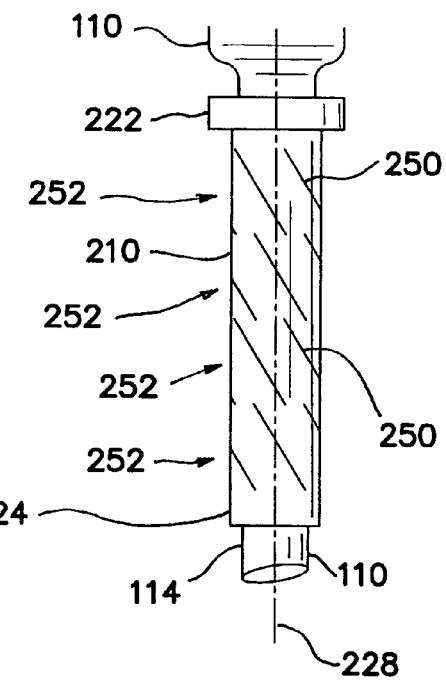
Figure 17C:
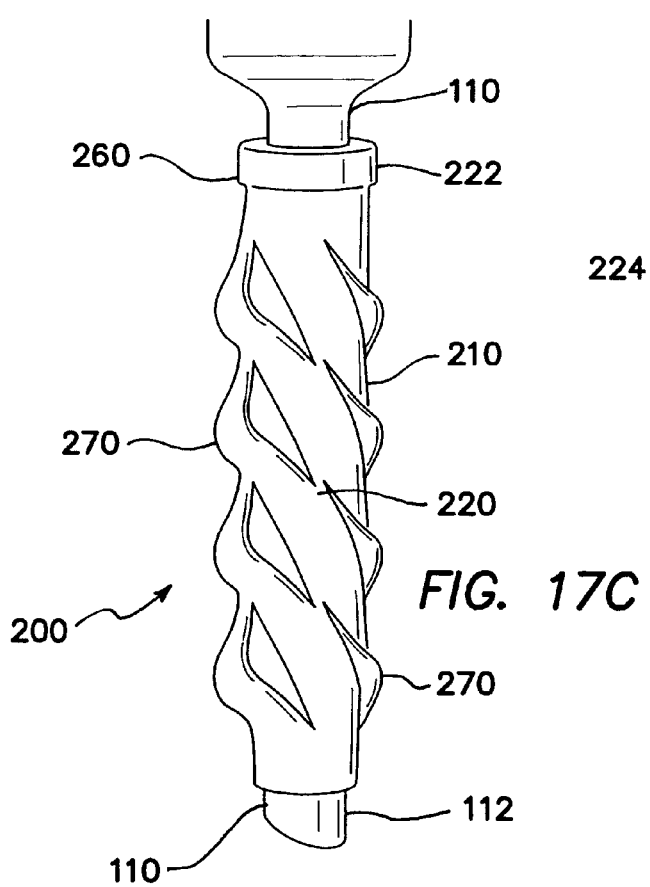
Figure 15D:
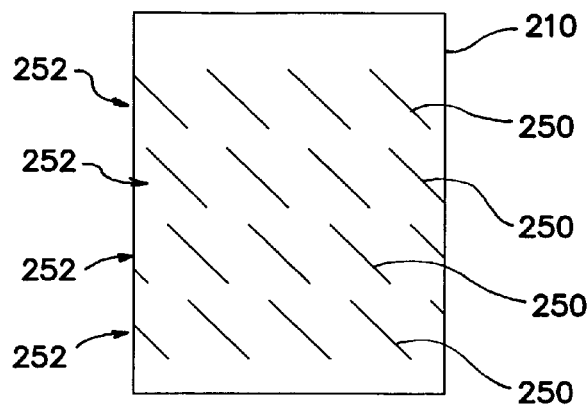
Figure 16D:
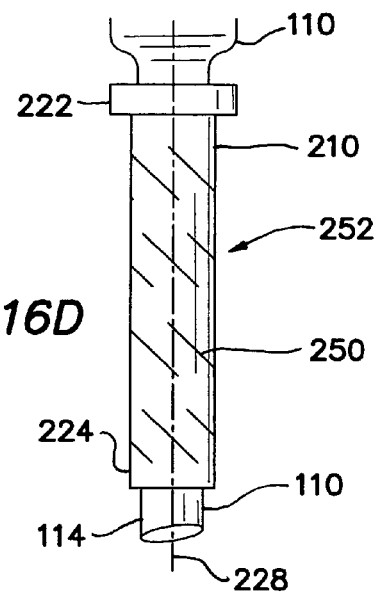
Figure 17D:
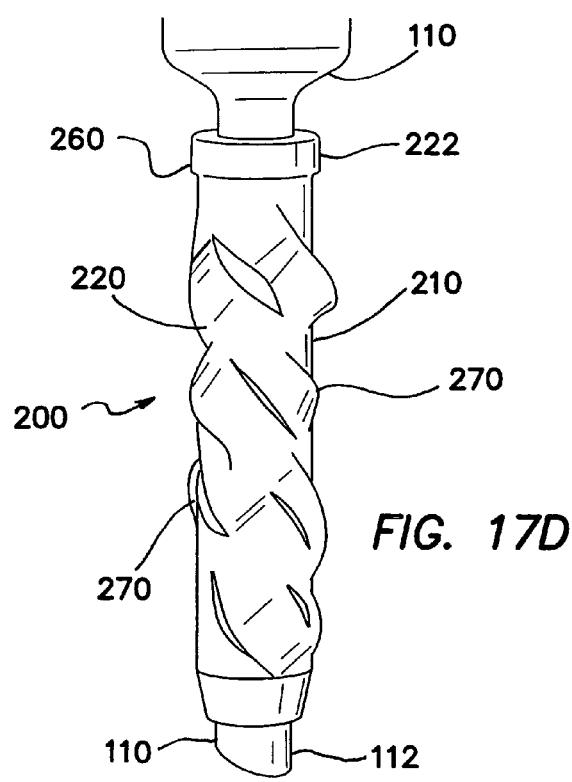
Figure 15E:
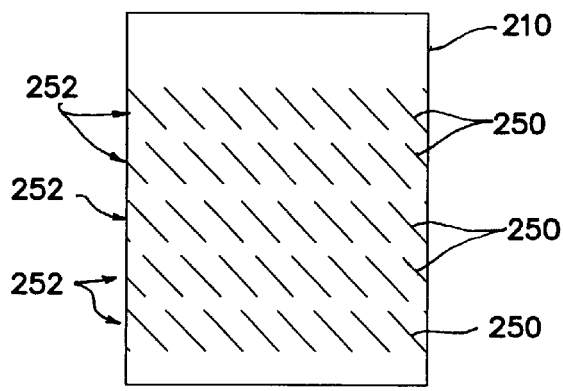
Figure 16E:
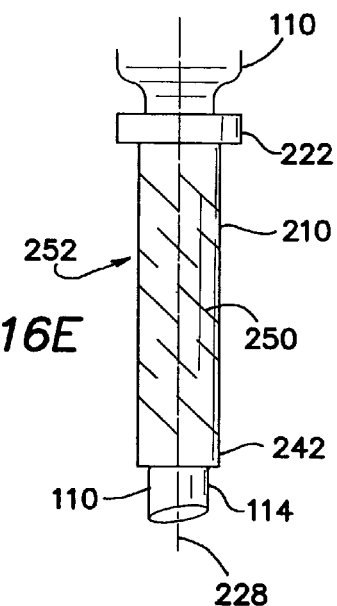
Figure 17E:
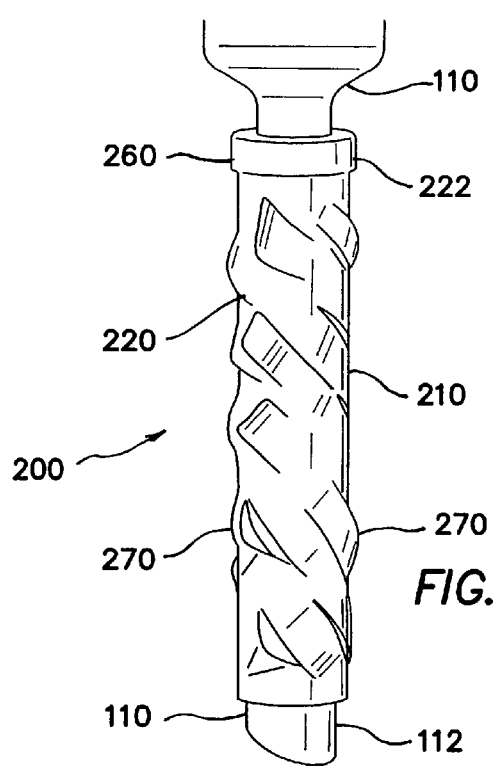
Figure 15F:
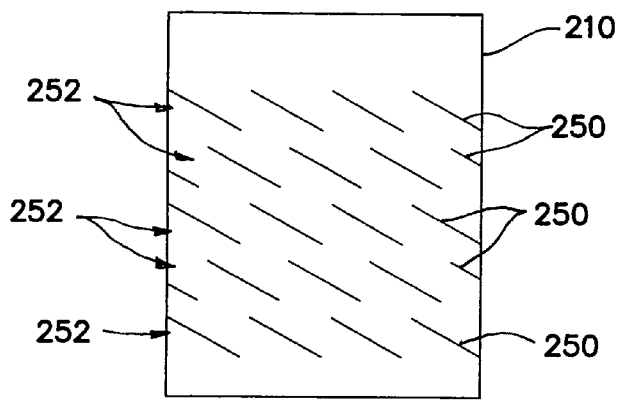
Figure 16F:
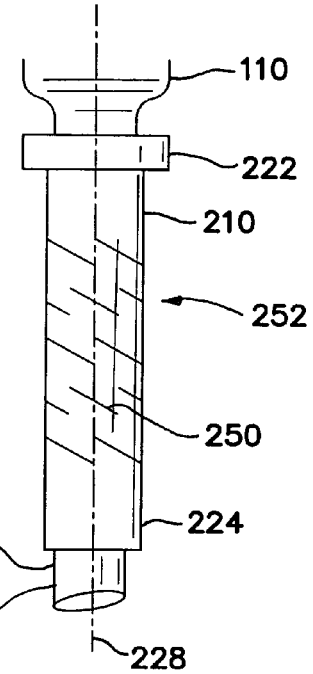
Figure 17F:
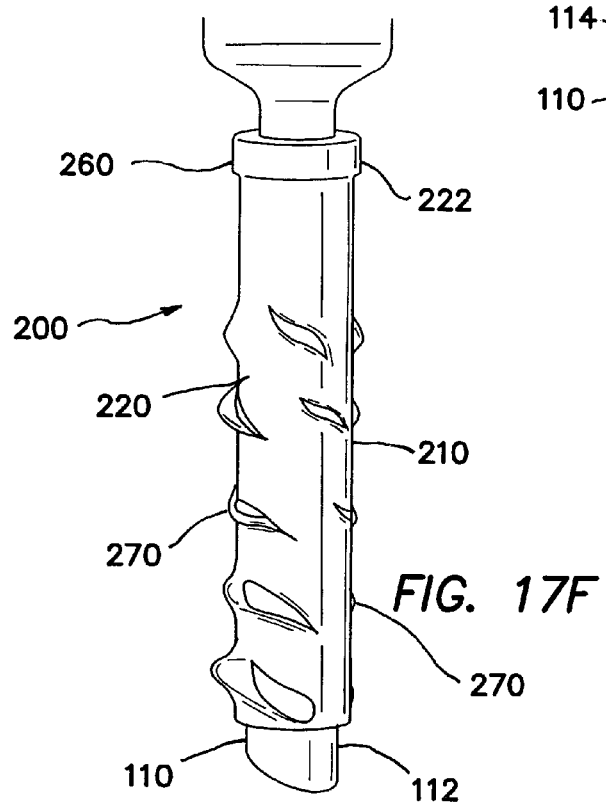
Figure 15G:
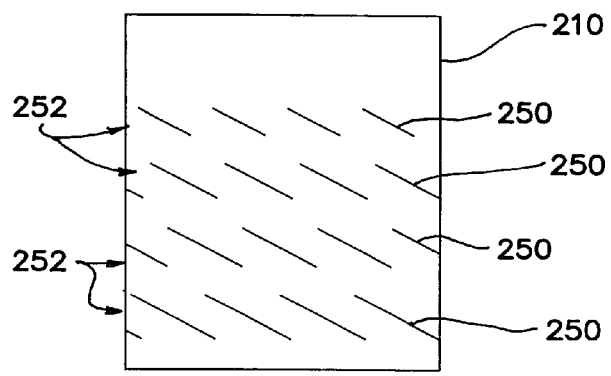
Figure 16G:
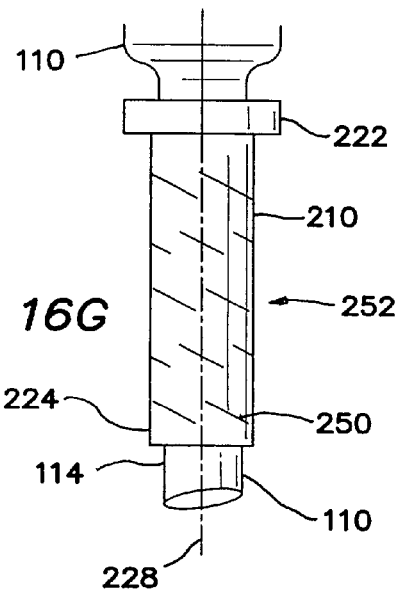
Figure 17G:
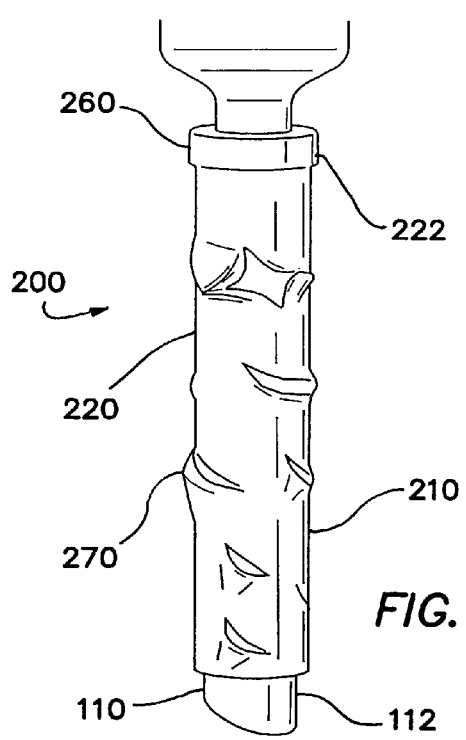
Figure 15H:
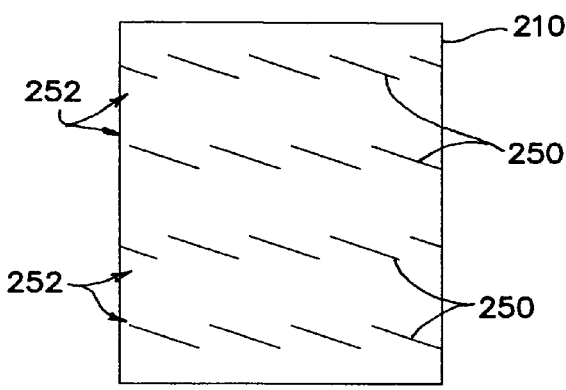
Figure 16H:
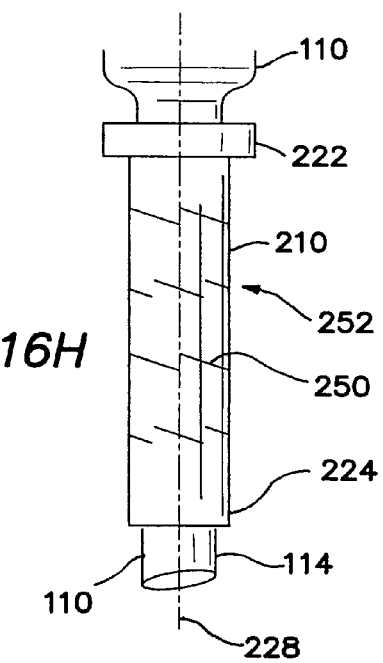
Figure 17H:
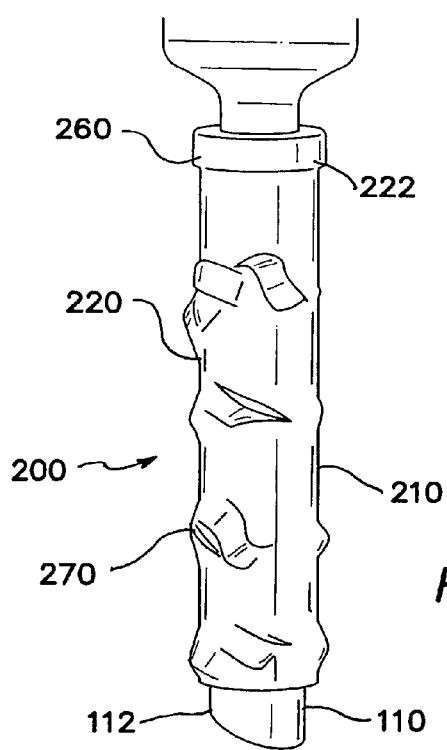
Figure 15I:
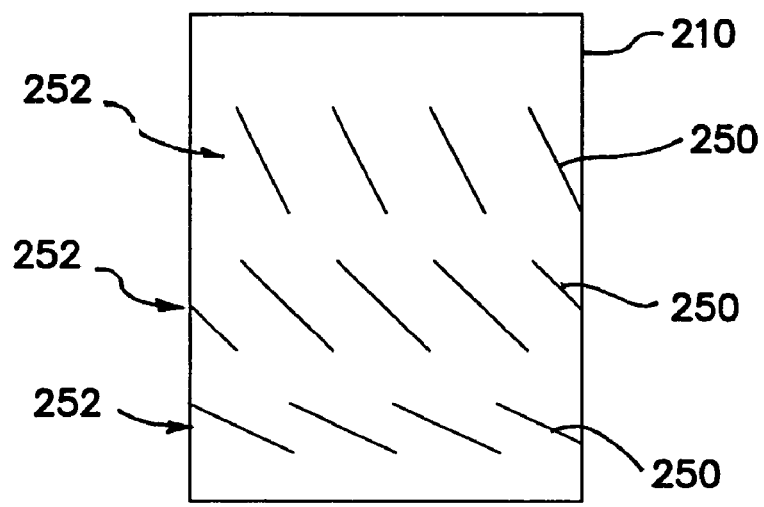
Figure 16I:
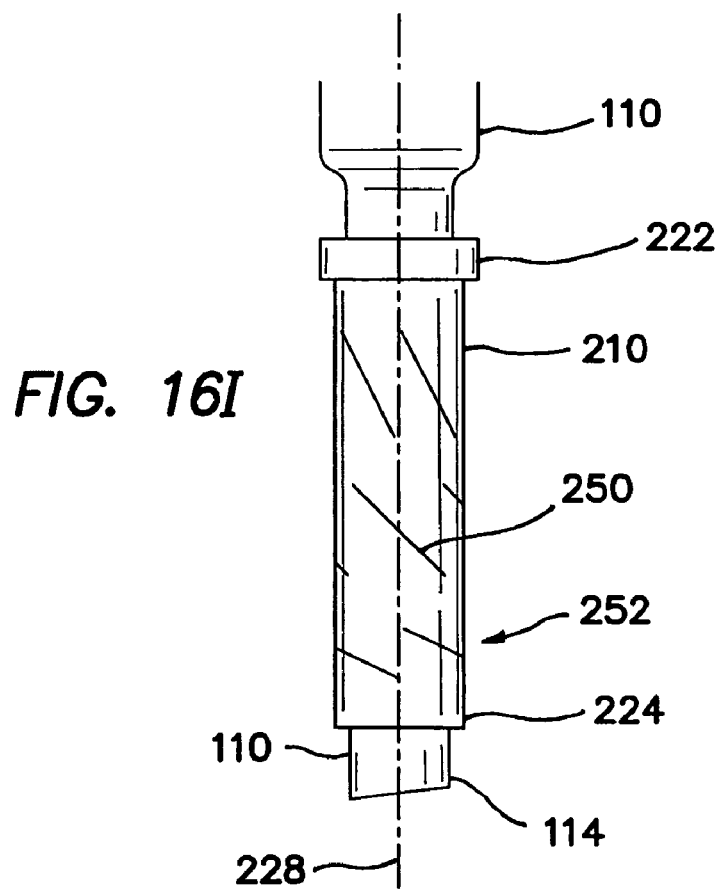

With continuing reference to FIG. 13, the elongate tube 210 includes a plurality of slits 250 positioned about a periphery within the central region 226 of the elongate tube, thereby forming a row 252 of slits within the central region. In one embodiment, there may be a plurality of rows 252 of slits 250 along the length of the central region 226 of the elongate tube 210. Referring to FIGS. 15a-15i and 16a-16i, the slits 250 within a row 252 may be substantially parallel to each other and may be either of substantially equal lengths (see FIGS. 15a-15f and 15h) or of different lengths (see FIG. 15g). The slits 250 are cut at an angle to the longitudinal axis 228 of the elongate tube 210. In one embodiment, the slits 250 may be at any angle between about 20° and about 70° to the longitudinal axis 228 of the elongate tube 210, however, those familiar in the art will recognize that other angles for the slits will produce successful results and are contemplated as within the scope of the present invention. Since the slits 250 are cut into a substantially cylindrical surface and are cut at an angle to the longitudinal axis 228, the slits have a substantially helical form. Alternatively, the slits 250 may be of varying lengths (see FIG. 15g) and/or at varying angles (see FIG. 15i) in relation to the longitudinal axis 228 of the elongate tube 210. In one embodiment, the length of the slits 250 may be between about 8.0 mm to about 35.0 mm, however, those familiar in the art will recognize that other lengths for the slits will produce successful results and are contemplated as within the scope of the present invention. Although the slits 250 are depicted as being substantially linear, it is contemplated as part of the present invention that the slits may have other shapes. Adjacent rows 252 of slits 250 may be either substantially rotatably aligned (see FIGS. 15a and 15b) about the longitudinal axis 228 along the length of the elongate tube or rotatably offset (see FIGS. 15c-15g) about the longitudinal axis from each other.

Figure 18:
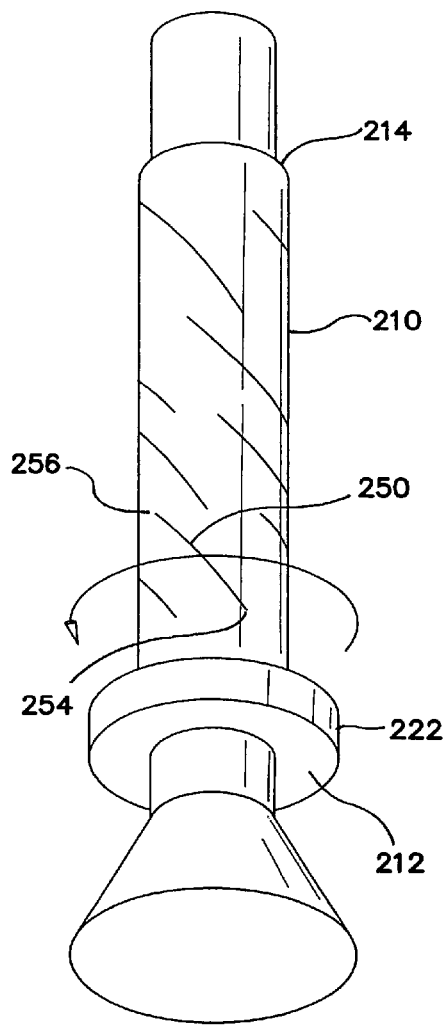
FIG. 18 is a perspective view of a trocar fixation device of the present invention mounted onto a cannula, the fixation device having helical slits extending distally in a counter-clockwise direction and depicting a direction of rotating the fixation device in order to activate the fixation device.
Figure 19:
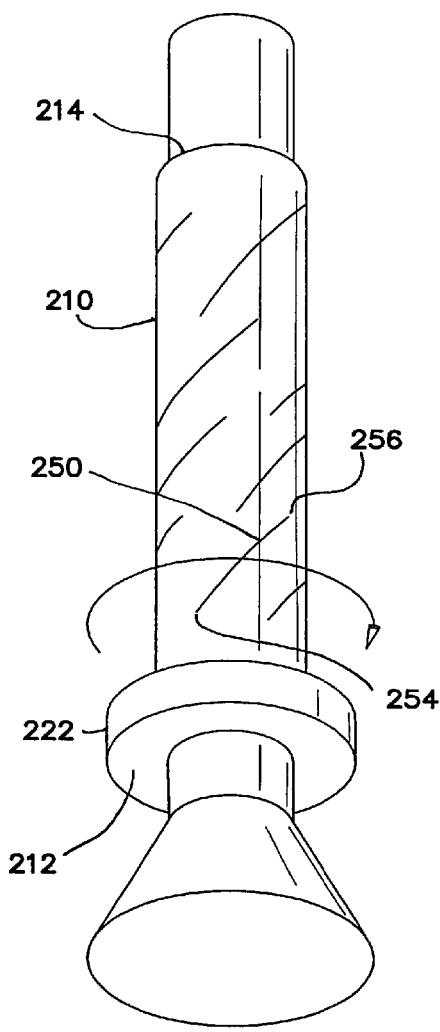
FIG. 19 is a perspective view of a trocar fixation device of the present invention mounted onto a cannula, the fixation device having helical slits extending distally in a clockwise direction and depicting a direction of rotating the fixation device in order to activate the fixation device.

With the elongate tube 210 installed onto the cannula 110 and the second, distal-end region 224 of the elongate tube coupled to the second, distal-end region 114 of the cannula or the central region 118 of the cannula, the fixation characteristics of the fixation device 200 are activated by rotating the first, proximal-end region 222 of the elongate tube in a first direction in relation to the cannula and about the longitudinal axis 228 of the elongate tube (see FIGS. 17a-17i). With reference to FIG. 18, when viewing the elongate tube 210 from the first, proximal end 212 looking toward the second, distal end 214, if the slits 250 extend counterclockwise from a proximal end 254 of the slit to a distal end 256 of the slit, then the first, proximal-end region 222 of the elongate tube is rotated in a first, counterclockwise direction to activate the fixation characteristics. Similarly, if the slits 250 extend clockwise from the proximal end 254 of the slit to the distal end 256 of the slit, then the first, proximal-end region 222 of the elongate tube is rotated in a first, clockwise direction to activate the fixation characteristics (see FIG. 19).

With reference to FIGS. 17a-17h, when the fixation device 200 is activated through rotation of the first, proximal-end region 222 of the elongate tube 210 in a first direction in relation to the cannula 110, the material of the elongate tube that is positioned between adjacent slits is compressed and forced radially outward away from the second, exterior surface 112 of the cannula, thereby forming ridges 270. When the first proximal-end region 222 of the elongate tube 210 is rotated in the second, opposite direction, the fixation device is deactivated and the second, exterior surface 220 of the elongate tube returns to a substantially smooth condition (see FIGS. 16a-16h). The first, proximal-end region 222 of the elongate tube 210 may include a handle portion 260 (see FIGS. 16a-16i) that enlarges the periphery of the first, proximal-end region to facilitate activation and deactivation of the fixation device 200. The handle portion 260 of the elongate tube 210 may either be an integral part of the elongate tube or be a separate piece coupled to the elongate tube.

Figure 20:
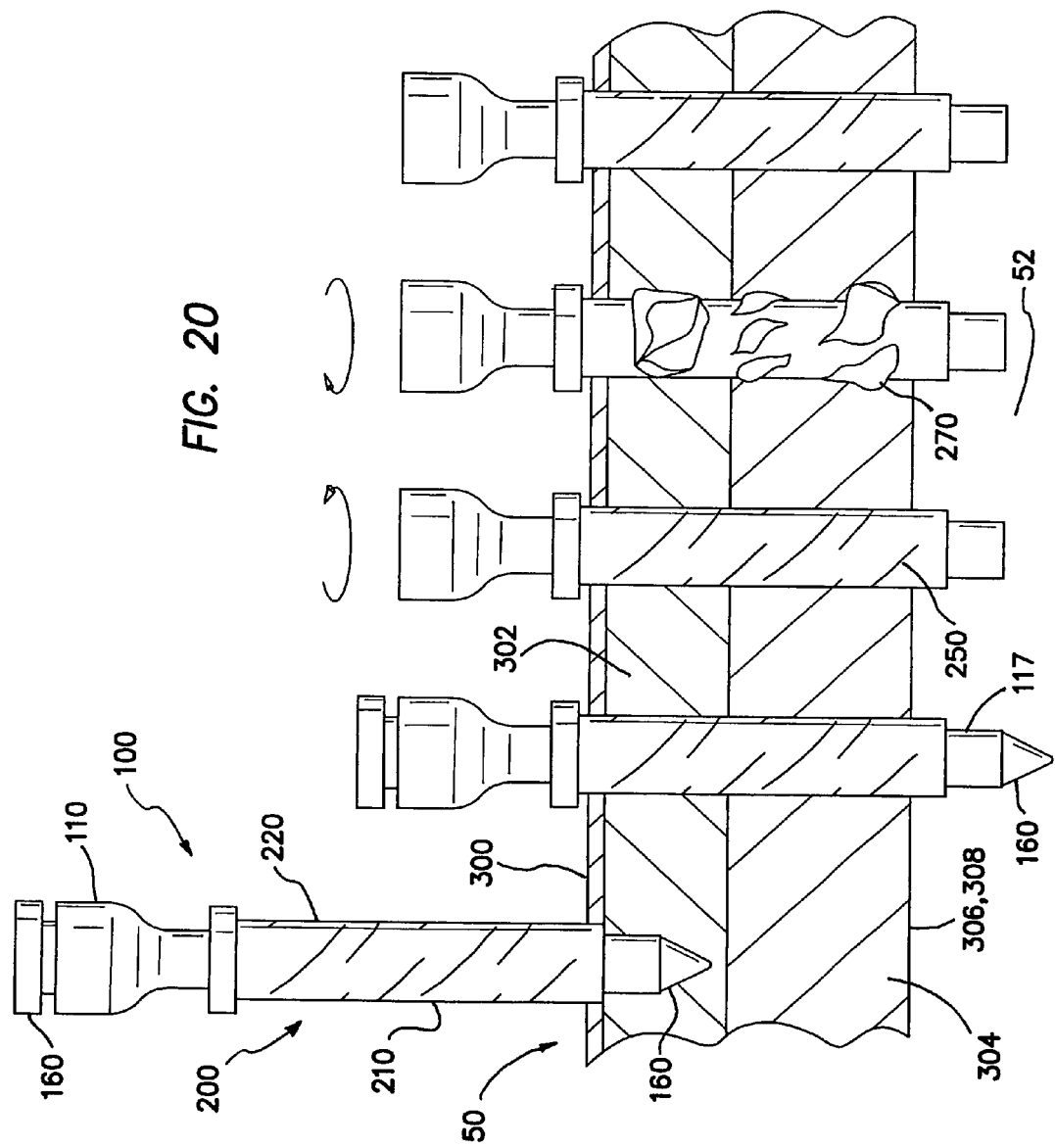
FIG. 20 is a side view, partially in cross-section, depicting the trocar fixation device of the present invention mounted onto a cannula and progressive steps of inserting the trocar into the body wall of a patient, activating the trocar fixation device and deactivating the trocar fixation device.

As depicted in FIG. 20, the body wall 50, such as the abdominal wall, includes skin 300, layers of muscle tissue 302, and a layer of connective tissue 304. Additionally, in the case of an abdominal wall, there is a final, internal membrane 306 referred to as the peritoneum 308. In use, the fixation device 200 of the present invention is part of a trocar 100. More particularly, the fixation device 200 is coupled to a cannula 110 as described above and a puncturing device, such as an obturator 160, is inserted into the lumen 130 of the cannula. With the fixation device 200 deactivated and the second, exterior surface 220 of the elongate tube 210 substantially smooth, the trocar 100 is pushed through the body wall 50 with a penetration force of sufficient magnitude to result in the penetration of the body wall. After achieving penetration of the body wall 50, the trocar 100 is advanced at least until a portion of the second, distal-end region 117 of the cannula is positioned within the body cavity 52 while the distal-most slits 250 on the elongate tube 210 are positioned within the body wall and not within the body cavity. With the fixation device 200 positioned in this manner, the fixation device may be activated as described above. The activation of the fixation device 200 causes the ridges 270 on the fixation device to deploy into the tissue of the body wall 50, thereby substantially preventing any proximal or distal movement between the elongate tube 210 and the body wall. Prior to removing the cannula 110 from the body wall 50, the fixation device 200 is deactivated as described above, thereby causing the second, exterior surface 220 of the elongate tube 210 to return to a substantially smooth condition and reducing the potential to cause damage to the body wall during removal of the cannula.

In one embodiment, the elongate tube 210 may be made of polyethylene, nylon, or other polymeric materials having similar properties that are well known in the art. The elongate tube 210 may be fabricated through a molding process, extrusion process, or other process that is well known in the art for producing polymeric tubing. In another embodiment, the elongate tube may be made from a heat shrink polymer, such as polyolefin.

Figure 21:
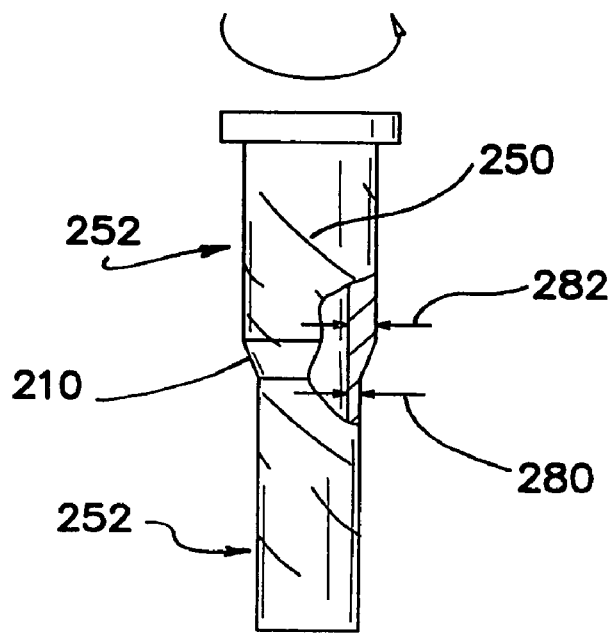
FIG. 21 is a side view of a trocar fixation device of the present invention, the trocar fixation device having varying thicknesses to facilitate progressive deployment of the fixation device.
Figure 22:
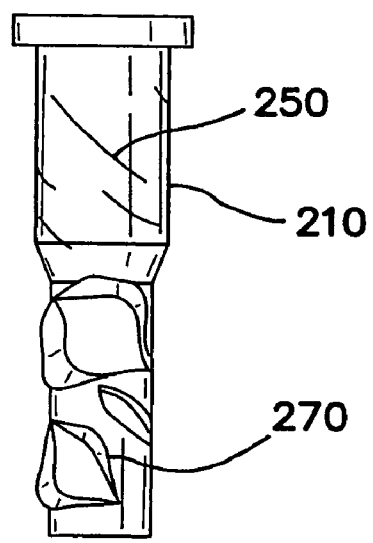
FIG. 22 is a side view of the trocar fixation device of FIG. 21 depicting the progressive deployment of the trocar fixation device.

Referring to FIGS. 21-22, another embodiment of the invention includes progressive deployment of the ridges 270 of the elongate tube 210. Progressive deployment of the ridges 270 is achieved by varying the thickness of the elongate tube 210 along its length such that at least one row 252 of slits 250 has a different thickness than an adjacent row of slits. More particularly, at least one row 252 of slits 250 is positioned within a region of the elongate tube 210 having a first thickness 280 and at least one other row 252 of slits 250 is positioned within a region of the elongate tube having a different, second thickness 282. The varying thickness may be achieved by molding different regions of the elongate tube 210 with different thicknesses, by layering portions of the elongate tube, or by any other means well known in the art. Alternatively, progressive deployment of the ridges 270 may be achieved by varying the stiffness of the elongate tube 210 along its length or by varying the slit 250 patterns from one row 252 to an adjacent row (see FIG. 16i).

Figure 23:
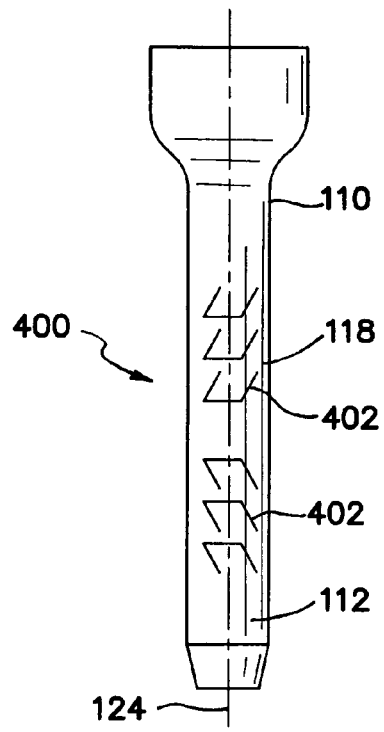
FIG. 23 is a side view of a trocar fixation device of the present invention mounted onto a cannula, the trocar fixation device having flaps that bias radially outwardly from an external surface of the cannula.

Referring to FIG. 23, in another embodiment of the invention, the fixation device 400 includes a at least one flap 402 coupled to a cannula 110 on the second, exterior surface 112 within the central region 118 of the cannula 110. In one embodiment, the fixation device 400 includes a plurality of flaps 402. In a free, activated state, the at least one flap 402 biases radially outwardly from the cannula 110 and in a constrained, deactivated state, the at least one flap is maintained substantially parallel to the second, exterior surface 112 of the cannula. In one embodiment, a plurality of flaps 402 may be aligned substantially parallel to a longitudinal axis 124 of the cannula 110. Alternatively, a plurality of flaps 402 may be arranged in other patterns, such as a helical pattern, an annular pattern, a serpentine pattern, or any other pattern that is well known in the art. In one embodiment, the at least one flap 402 may include a parallelogram shape as depicted in FIG. 23. In other embodiments, the at least one flap 402 may include other shapes, such as triangular, rectangular, square, other polygonal shapes, or curved.

Figure 24:
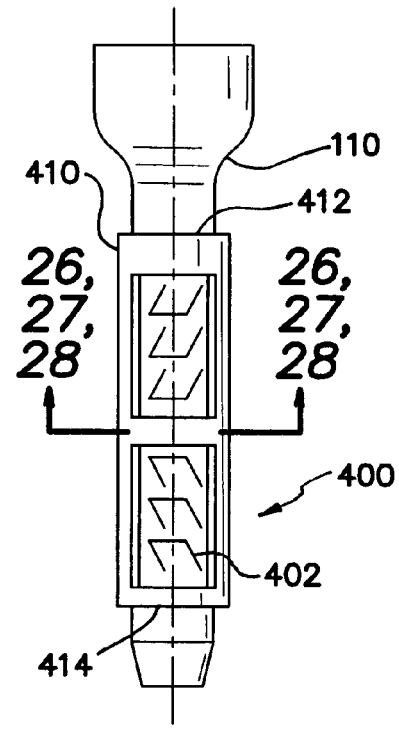
FIG. 24 is a side view of the trocar fixation device of FIG. 23, further depicting an elongate tube mounted onto the cannula and exposing the flaps of the trocar fixation device.
Figure 25:
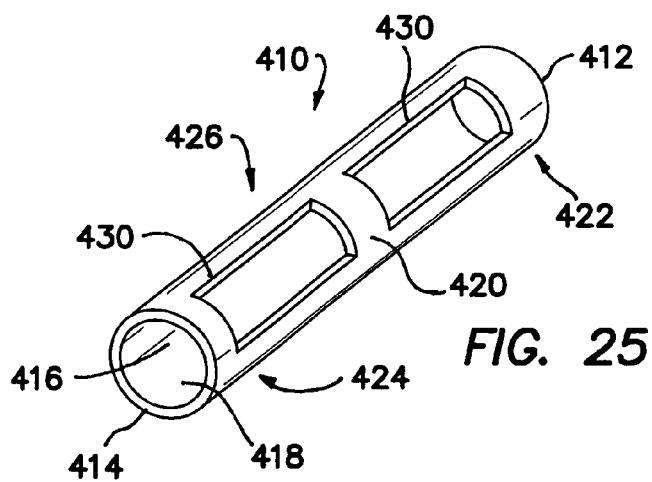
FIG. 25 is a perspective view of the elongate tube of FIG. 24.

Referring to FIGS. 24 and 25, to maintain the at least one flap 402 in the constrained, deactivated state, the fixation device 400 includes an elongate tube 410 that is rotatably mounted onto the cannula 110 and over the at least one flap. The elongate tube 410 includes a first, proximal end 412, a second, distal end 414, a lumen 416 extending between the proximal end and the distal end, a first, interior surface 418, and a second, exterior surface 420. The elongate tube 410 may also include a first, proximal-end region 422, a second, distal-end region 424, and a central region 426 that is positioned between the proximal-end region and the distal-end region. The elongate tube 410 further includes at least one opening 430 that extends between the first, interior surface 418 and the second, exterior surface 420 of the elongate tube 410. The at least one opening 430 is sized and positioned such that rotation of the elongate tube 410 in a first direction about the cannula 110 exposes at least one entire flap 402 through the at least one opening and allows the at least one flap to activate by protruding radially away from the second, exterior surface 112 of the cannula. In one embodiment, the at least one opening 430 may be positioned within the central region 426 of the elongate tube 410. The elongate tube 410 may be fabricated of polyethylene or any other material well known in the art that may be used for surgical purposes and that possesses sufficient stiffness to collapse the at least one flap 402 during deactivation of the fixation device 400.

Figure 26:
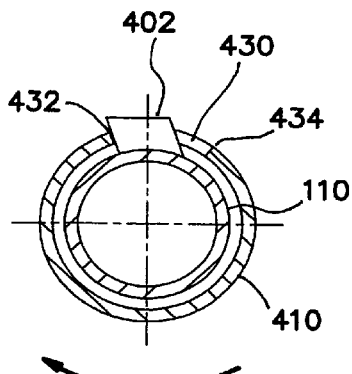
FIG. 26 is a section view taken from line 26-26 in FIG. 24 depicting the trocar fixation device in the activated condition.
Figure 27:
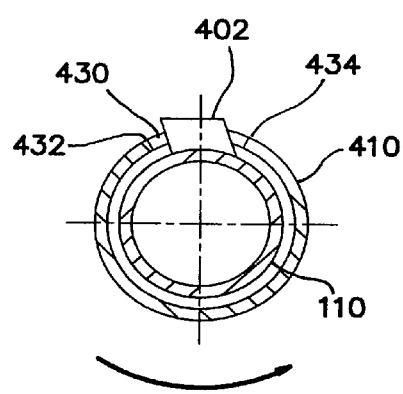
FIG. 27 is a section view taken from line 27-27 in FIG. 24 depicting the trocar fixation device in the activated condition with the elongate tube being rotated to deactivate the trocar fixation device.
Figure 28:
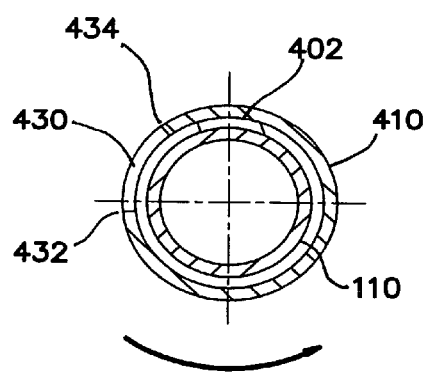
FIG. 28 is a section view taken from line 28-28 in FIG. 24 depicting the trocar fixation device in the deactivated condition.

Referring to FIG. 26, with the at least one flap 402 having a substantially parallelogram shape, continued rotation of the elongate tube 410 in the first direction causes a first edge 432 of the at least one opening 430 to be positioned under a portion of the at least one activated flap and substantially supports the at least one flap in the activated state. Rotating the elongate tube in a second direction (see FIG. 27), substantially opposite the first direction, about the cannula 110 removes support for the at least one flap. With continued rotation of the elongate tube 410 in the second direction (see FIG. 28), a second edge 434 of the at least one opening 430 slides over the at least one flap 402 to collapse and deactivate the at least one flap.

The at least one flap 402 may be fabricated through any of numerous available means. In one embodiment, the at least one flap 402 may be cut into a sleeve, such as a polymeric sleeve, the flap bent outwardly away from the sleeve, and the sleeve subsequently coupled to the central region 118 of the cannula 110. In another embodiment, the at least one flap 402 may be overmolded onto the central region 118 of the cannula 110. In another embodiment, the at least one flap 402 may be formed in a strip of material that is subsequently coupled to the central region 118 of the cannula 110. The at least one flap 402 may also be formed through any other means well known in the art and coupled to the central region 118 of the cannula 110 through any other means well known in the art. The at least one flap 402 may be formed of polyethylene or any other material well known in the art that may be used for surgical purposes and that possesses properties of shape memory and flexibility.

Referring to FIG. 29, in use, the fixation device 400 of the present invention is part of a trocar 100. More particularly, the fixation device 400 is coupled to a cannula 110 as described above and a puncturing device, such as an obturator 160, is inserted into the lumen 130 of the cannula. With the fixation device 400 deactivated and the second, exterior surface 420 of the elongate tube 410 substantially smooth, the trocar 100 is pushed through the body wall 50 with a penetration force of sufficient magnitude to result in the penetration of the body wall. After achieving penetration of the body wall 50, the trocar 100 is advanced until at least a portion of the second, distal-end region 117 of the cannula is positioned within the body cavity 52 while the elongate tube 410 is positioned within the body wall and not within the body cavity. With the fixation device 400 positioned in this manner, the fixation device may be activated as described above. The activation of the fixation device 400 causes the at least one flap 402 on the activation device to deploy into the tissue of the body wall 50, thereby substantially preventing any proximal or distal movement between the fixation device 400 and the body wall. Prior to removing the cannula 110 from the body wall 50, the fixation device 400 is deactivated as described above, thereby causing the fixation device 400 to return to a substantially smooth condition and reducing the potential to cause damage to the body wall during removal of the cannula.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of many embodiments. Those skilled in the art will envision other modifications within the scope and spirit of the present invention as defined by the following claims.

The invention claimed is:

1. A trocar fixation device, comprising:
   an elongate tube that is mountable onto the exterior of a cannula, the elongate tube having a first, proximal end, a second, distal end, a lumen extending between the first, proximal end and the second, distal end the lumen sized and configured to receive an exterior surface of the cannula, a first, generally cylindrical interior surface defined by the lumen, a second, generally cylindrical exterior surface having a substantially constant diameter from the proximal end to the distal end of the elongate tube, a first, proximal-end region, a second, distal-end region, a central region positioned between the first, proximal-end region and the second, distal-end region, and a plurality of slits positioned about a periphery of the central region of the elongate tube and forming a row of slits,
   wherein the elongate tube is actuatable between an activated position in which the elongate tube comprises the lumen extending between the proximal end and the distal end, the generally cylindrical interior surface defined by the lumen, and the generally cylindrical exterior surface having the substantially constant diameter extending continuously and remaining continuous from the proximal end to the distal end of the elongate tube and wherein the slits define ridges protruding from the generally cylindrical exterior surface of the elongate tube and a deactivated position in which the generally cylindrical exterior surface of the elongate tube is substantially smooth and has the substantially constant diameter extending continuously and remaining continuous from the proximal end to the distal end of the elongate tube.

2. The trocar fixation device of claim 1, further comprising a plurality of rows of slits within the central region of the elongate tube.

3. The trocar fixation device of claim 2, wherein adjacent rows of slits are substantially rotatably aligned about a longitudinal axis of the elongate tube.

4. The trocar fixation device of claim 2, wherein adjacent rows of slits are rotatably offset about a longitudinal axis of the elongate tube.

5. The trocar fixation device of claim 1, the plurality of slits being substantially parallel to each other.

6. The trocar fixation device of claim 1, the plurality of slits being of substantially equal length.

7. The trocar fixation device of claim 1, wherein at least two of the slits are of different lengths.

8. The trocar fixation device of claim 1, wherein the slits are cut at an angle to a longitudinal axis of the elongate tube.

9. The trocar fixation device of claim 8, wherein the slits are cut at an angle of between about 20° and about 70° to the longitudinal axis of the elongate tube.

10. The trocar fixation device of claim 8, wherein at least two of the slits are not parallel to each other.

11. The trocar fixation device of claim 1, the slits having a substantially helical form.

12. The trocar fixation device of claim 1, the slits having a length of between about 8.0 mm and about 35.0 mm.

13. The trocar fixation device of claim 1, further comprising:
   a cannula having a first, interior surface, a second, exterior surface, a first, proximal end, a second, distal end, a lumen extending between the proximal end and the distal end, a first, proximal-end region, a second, distal-end region, and a central region that is positioned between the proximal-end region and the distal-end region;
   the cannula being positioned within the lumen of the elongate tube such that the second, distal end of the cannula extends distally beyond the second, distal end of the elongate tube; and at least a portion of the second, distal-end region of the elongate tube being coupled to the second, exterior surface of the cannula forming a substantially gas-tight seal between the elongate tube and the cannula.

14. The trocar fixation device of claim 13, wherein at least a portion of the second, distal-end region of the elongate tube is coupled to the second, distal-end region of the cannula.

15. The trocar fixation device of claim 13, wherein at least a portion of the second, distal-end region of the elongate tube is coupled to the central region of the cannula.

16. The trocar fixation device of claim 13, wherein the trocar fixation device is activated by rotating the first, proximal-end region of the elongate tube in a first direction in relation to the cannula and about a longitudinal axis of the elongate tube and the trocar fixation device is deactivated by rotating the first, proximal-end region of the elongate tube in a second direction, opposite to the first direction, in relation to the cannula and about the longitudinal axis of the elongate tube.

17. The trocar fixation device of claim 16, wherein:
   activation of the trocar fixation device compresses the material positioned between adjacent slits and forces the material between adjacent slits radially outwardly, away from the second, exterior surface of the cannula, thereby forming the ridges in the second, exterior surface of the elongate tube; and
   deactivation of the trocar fixation device returns the second, exterior surface of the elongate tube to the substantially smooth condition.

18. The trocar fixation device of claim 1, further comprising:
   a plurality of rows of slits within the central region of the elongate tube;
   wherein at least one row of slits has a different thickness than an adjacent row of slits.

19. The trocar fixation device of claim 1, further comprising:
   a plurality of rows of slits within the central region of the elongate tube;
   wherein at least one row of slits has a different stiffness than an adjacent row of slits.

20. The trocar fixation device of claim 1, further comprising:
   a plurality of rows of slits within the central region of the elongate tube;
   wherein at least one row of slits has a different slit pattern than an adjacent row of slits.

21. A trocar fixation device for selectively securing a trocar across a body wall having an outer surface, an inner surface, and an incision therethrough, comprising:
   a cannula having a first, interior surface, a second, exterior surface, a first, proximal end, a second, distal end, a first, proximal-end region, a second, distal-end region, and a central region that is positioned between the proximal-end region and the distal-end region; and
   an elongate tube that is mountable onto the second, exterior surface of the cannula, the elongate tube having a first, proximal end, a second, distal end, a lumen extending between the first, proximal end and the second, distal end, a first, interior surface, a second, exterior surface defining a generally cylindrical tubular body having a substantially constant diameter extending continuously and remaining continuous from the proximal end to the distal end, a first, proximal-end region, a second, distal-end region, a central region positioned between the first, proximal-end region and the second, distal-end region and a plurality of slits positioned about a periphery of the central region of the elongate tube and forming a row of slits, the slits being cut at an angle to a longitudinal axis of the elongate tube, the plurality of slits being actuatable between an activated position in which the slits define ridges protruding radially outward from the generally constant diameter of the generally cylindrical tubular body extending continuously and remaining continuous from the proximal end to the distal end of the elongate tube; and a deactivated position in which the exterior surface of the elongate tube defining the generally cylindrical tubular body having the substantially constant diameter extending continuously and remaining continuous from the proximal end to the distal end is substantially smooth;
   wherein the cannula is positioned within the lumen of the elongate tube such that the second, distal end of the cannula extends distally beyond the second, distal end of the elongate tube; and
   at least a portion of the second, distal-end region of the elongate tube being coupled to the second, exterior surface of the cannula forming a substantially gas-tight seal between the elongate tube and the cannula.

22. The trocar fixation device of claim 21, further comprising a plurality of rows of slits within the central region of the elongate tube.

23. The trocar fixation device of claim 22, wherein adjacent rows of slits are substantially rotatably aligned about a longitudinal axis of the elongate tube.

24. The trocar fixation device of claim 22, wherein adjacent rows of slits are rotatably offset about a longitudinal axis of the elongate tube.

25. The trocar fixation device of claim 21, the plurality of slits being substantially parallel to each other.

26. The trocar fixation device of claim 21, wherein at least two of the slits are not parallel to each other.

27. The trocar fixation device of claim 21, wherein the slits are cut at an angle of between about 20° and about 70° to the longitudinal axis of the elongate tube.

28. The trocar fixation device of claim 21, the plurality of slits being of substantially equal length.

29. The trocar fixation device of claim 21, wherein at least two of the slits are of different lengths.

30. The trocar fixation device of claim 21, the slits having a length of between about 8.0 mm and about 35.0 mm.

31. The trocar fixation device of claim 21, wherein at least a portion of the second, distal-end region of the elongate tube is coupled to the second, distal-end region of the cannula.

32. The trocar fixation device of claim 21, wherein at least a portion of the second, distal-end region of the elongate tube is coupled to the central region of the cannula.

33. The trocar fixation device of claim 21, wherein the trocar fixation device is activated by rotating the first, proximal-end region of the elongate tube in a first direction in relation to the cannula and about a longitudinal axis of the elongate tube and the trocar fixation device is deactivated by rotating the first, proximal-end region of the elongate tube in a second direction, opposite to the first direction, in relation to the cannula and about the longitudinal axis of the elongate tube.

34. The trocar fixation device of claim 33, wherein:
   activation of the trocar fixation device compresses the material positioned between adjacent slits and forces the material between adjacent slits radially outwardly, away from the second, exterior surface of the cannula, thereby forming the ridges in the second, exterior surface of the elongate tube; and deactivation of the trocar fixation device returns the second, exterior surface of the elongate tube to the substantially smooth condition.

35. The trocar fixation device of claim 21, further comprising:
 a plurality of rows of slits within the central region of the elongate tube;
 wherein at least one row of slits has a different thickness than an adjacent row of slits.

36. The trocar fixation device of claim 21, further comprising:
 a plurality of rows of slits within the central region of the elongate tube;
 wherein at least one row of slits has a different stiffness than an adjacent row of slits.

37. The trocar fixation device of claim 21, further comprising:
 a plurality of rows of slits within the central region of the elongate tube;
 wherein at least one row of slits has a different slit pattern than an adjacent row of slits.

38. A trocar fixation device, comprising:
 a cannula having a first, interior surface, a second, exterior surface, a first, proximal end, a second, distal end, a first, proximal-end region, a second, distal-end region, and a central region that is positioned between the proximal-end region and the distal-end region; and
 an elongate tube that is mountable onto the second, exterior surface of the cannula, the elongate tube having a first, proximal end, a second, distal end, a lumen extending between the first, proximal end and the second, distal end, a first, interior surface, a second, generally cylindrical exterior surface having a substantially constant diameter extending continuously and remaining continuous from the proximal end to the distal end of the elongate tube, a first, proximal-end region, a second, distal-end region, a central region positioned between the first, proximal-end region and the second, distal-end region, and a plurality of slits positioned about a periphery of the central region of the elongate tube and forming a row of slits, the slits being cut at an angle to a longitudinal axis of the elongate tube;
 wherein the cannula is positioned within the lumen of the elongate tube such that the second, distal end of the cannula extends distally beyond the second, distal end of the elongate tube;
 at least a portion of the second, distal-end region of the elongate tube being coupled to the second, exterior surface of the cannula forming a substantially gas-tight seal between the elongate tube and the cannula;
 the slits are cut at an angle of between about 20° and about 70° to the longitudinal axis of the elongate tube;
 the slits having a length of between about 8.0 mm and about 35.0 mm, the length of the slits being significantly shorter than a length defined between the proximal end and the distal end of the elongate tube;
 the trocar fixation device is activated by rotating the first, proximal-end region of the elongate tube in a first direction in relation to the cannula and about a longitudinal axis of the elongate tube and the trocar fixation device is deactivated by rotating the first, proximal-end region of the elongate tube in a second direction, opposite to the first direction, in relation to the cannula and about the longitudinal axis of the elongate tube;
 activation of the trocar fixation device compresses the material positioned between adjacent slits and forces the material between adjacent slits radially outwardly, away from the second, exterior surface of the cannula, thereby forming ridges in the second, exterior surface of the elongate tube, the slits being dimensioned and spaced such that upon activation of the trocar fixation device, the exterior surface of the elongate tube remains generally cylindrical having the substantially constant diameter extending continuously and remaining continuous from the proximal end to the distal end of the elongate tube punctuated by the ridges extending therefrom; and
 deactivation of the trocar fixation device returns the second, generally cylindrical exterior surface of the elongate tube to a substantially smooth condition having the substantially constant diameter extending continuously and remaining continuous from the proximal end to the distal end of the elongate tube.

39. The trocar fixation device of claim 38, further comprising a plurality of rows of slits within the central region of the elongate tube.

40. The trocar fixation device of claim 38, the plurality of slits being substantially parallel to each other.

41. The trocar fixation device of claim 38, wherein at least two of the slits are not parallel to each other.

42. The trocar fixation device of claim 38, the plurality of slits being of substantially equal length.

43. The trocar fixation device of claim 38, wherein at least two of the slits are of different lengths.

44. The trocar fixation device of claim 38, further comprising:
 a plurality of rows of slits within the central region of the elongate tube;
 wherein at least one row of slits has a different thickness than an adjacent row of slits.

45. The trocar fixation device of claim 38, further comprising:
 a plurality of rows of slits within the central region of the elongate tube;
 wherein at least one row of slits has a different stiffness than an adjacent row of slits.

46. The trocar fixation device of claim 38, further comprising:
 a plurality of rows of slits within the central region of the elongate tube;
 wherein at least one row of slits has a different slit pattern than an adjacent row of slits.

47. A trocar fixation device, comprising:
 an elongate tube that is mountable onto the exterior of a cannula, the elongate tube having a proximal end, a distal end, a generally cylindrical tubular body having a first diameter extending continuously between the proximal end and the distal end and a length between the proximal end and the distal end, and a plurality of slits positioned about a periphery of the elongate tube;
 wherein the elongate tube is actuatable between an activated position in which the slits define ridges in the generally cylindrical tubular body, the ridges defining a second diameter greater than the first diameter, such that the elongate tube has an exterior surface defined by segments of the generally cylindrical tubular body having the first diameter extending continuously and remaining continuous between the proximal end and the distal end punctuated by the ridges having the second diameter, and a deactivated position in which the elongate tube has an exterior surface defined by the tubular body having the first diameter extending continuously and remaining continuous between the proximal end and the distal end.

48. The trocar fixation device of claim 47, wherein the plurality of slits is positioned in a plurality of rows of slits.

49. The trocar fixation device of claim 48, wherein the elongate tube is configured such that one row of slits of the plurality of rows of slits is arranged to be progressively deployed before another row of slits of the plurality of rows of slits.

50. The trocar fixation device of claim 49, wherein the elongate tube has a first thickness for the row of slits arranged to be progressively deployed before another row of slits and a second thickness for the other row of slits.

51. The trocar fixation device of claim 47, wherein each of the slits of the plurality of slits extend substantially less than the length of the generally cylindrical tubular body such that each of the ridges formed in the activated position extends substantially less than the length of the generally cylindrical tubular body.

52. The trocar fixation device of claim 51, wherein at least two of the slits extend at different transverse angles.

53. The trocar fixation device of claim 47, wherein each of the slits of the plurality of slits has a length and at least two of the slits have different lengths.

54. The trocar fixation device of claim 47, wherein the elongate tube defines a longitudinal axis and wherein each of the slits of the plurality of slits extends at a transverse angle to the longitudinal axis.

55. A trocar fixation device, comprising:
an elongate tube positionable on the exterior of a cannula, the elongate tube having a proximal end and a distal end and an exterior surface, the exterior surface comprising:
a plurality of expandable portions positioned between the proximal end and the distal end of the elongate tube, and;
a plurality of non-expandable portions extending continuously and remaining continuous from the proximal end to the distal end of the elongate tube;
wherein the plurality of expandable portions are actuatable from a retracted position to an expanded position upon rotation of the proximal end relative to the distal end, and wherein the non-expandable portions remain substantially undisturbed upon rotation of the proximal end relative to the distal end, the non-expandable portions having a generally tubular profile extending continuously and remaining continuous from the proximal end to the distal end of the elongate tube.

56. The trocar fixation device of claim 55, wherein the expandable portions are pivotally actuatable from the retracted position to the expanded position such that an edge of each of the expandable portions maintains contact with an adjacent non-expandable portion and an opposite edge of each of the expandable portions extends radially outward from the exterior surface of the elongate tube.

57. The trocar fixation device of claim 56, wherein the elongate tube further comprises a plurality of slits formed therein, the plurality of slits defining the plurality of expandable portions of the exterior surface.

58. The trocar fixation device of claim 57, wherein the each slit of the plurality of slits defines the opposite edge of the each expandable portion.

59. The trocar fixation device of claim 55, wherein the plurality of expandable portions are spaced in a plurality of rows of expandable portions on the exterior surface.

60. The trocar fixation device of claim 55, wherein the plurality of expandable portions are spaced irregularly on the exterior surface.

61. The trocar fixation device of claim 55, wherein the exterior surface of the elongate tube has a surface area and wherein the expandable portions define a small proportion of the surface area relative to the non-expandable portions.

62. The trocar fixation device of claim 55, wherein the non-expandable portions define a generally cylindrical inner surface extending from the proximal end to the distal end of the elongate tube and a generally cylindrical outer surface extending from the proximal end to the distal end of the elongate tube opposite the generally cylindrical inner surface upon rotation of the proximal end relative to the distal end to actuate the expandable portions to the expanded position, and wherein the elongate tube is positionable on the cannula such that the generally cylindrical inner surface is positioned about the cannula continuously from the proximal end to the distal end of the elongate tube.

* * * * *